(12) United States Patent
Parikh et al.

(10) Patent No.: US 11,872,372 B2
(45) Date of Patent: Jan. 16, 2024

(54) IDENTIFICATION OF SITES FOR SENSING ARRANGEMENTS

(71) Applicant: Medtronic MiniMed, Inc., Northridge, CA (US)

(72) Inventors: Neha J. Parikh, West Hills, CA (US); Rebecca K. Gottlieb, Culver City, CA (US); Benyamin Grosman, Winnetka, CA (US); Anirban Roy, Agoura Hills, CA (US); Di Wu, Glendale, CA (US)

(73) Assignee: Medtronic MiniMed, Inc., Northridge (CA)

( * ) Notice: Subject to any disclaimer, the term of this patent is extended or adjusted under 35 U.S.C. 154(b) by 319 days.

(21) Appl. No.: 17/316,304

(22) Filed: May 10, 2021

(65) Prior Publication Data

US 2021/0268186 A1 Sep. 2, 2021

Related U.S. Application Data

(63) Continuation of application No. 16/224,697, filed on Dec. 18, 2018, now Pat. No. 11,027,064, which is a
(Continued)

(51) Int. Cl.
*A61M 5/172* (2006.01)
*A61B 5/145* (2006.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
CPC ............ A61M 5/1723; A61M 5/16877; A61M 2005/14208; G16H 40/63; G16H 50/70; G16H 10/60; A61B 5/4839; A61B 5/748
See application file for complete search history.

(56) References Cited

U.S. PATENT DOCUMENTS

| 3,631,847 A | 1/1972 | Hobbs, II |
| 4,212,738 A | 7/1980 | Henne |

(Continued)

FOREIGN PATENT DOCUMENTS

| DE | 4329229 | 3/1995 |
| EP | 0319268 | 11/1988 |

(Continued)

OTHER PUBLICATIONS

PCT Search Report (PCT/US02/03299), dated Oct. 31, 2002, Medtronic Minimed, Inc.
(Continued)

*Primary Examiner* — Bradley J Osinski
(74) *Attorney, Agent, or Firm* — Weaver Austin Villeneuve & Sampson LLP

(57) ABSTRACT

A processor-implemented method includes obtaining measurement data indicative of a physiological condition measured by a sensing arrangement located at a site on a body, determining a lag associated with the sensing arrangement based on a relationship between the measurement data and reference data, and identifying, based on the lag, the site at which the sensing arrangement is located from a plurality of sites on the body.

20 Claims, 11 Drawing Sheets

Related U.S. Application Data continuation of application No. 15/240,720, filed on Aug. 18, 2016, now Pat. No. 10,201,657.

(60) Provisional application No. 62/208,486, filed on Aug. 21, 2015.

(51) Int. Cl.

| | | |
|---|---|---|
| *A61M 5/142* | (2006.01) | |
| *G16H 40/63* | (2018.01) | |
| *G16H 20/17* | (2018.01) | |
| *G16Z 99/00* | (2019.01) | |
| *A61B 5/00* | (2006.01) | |
| *A61M 5/168* | (2006.01) | |
| *G16H 10/60* | (2018.01) | |
| *G16H 50/70* | (2018.01) | |

(52) U.S. Cl.
CPC .... *A61M 5/14244* (2013.01); *A61M 5/16877* (2013.01); *G16H 10/60* (2018.01); *G16H 20/17* (2018.01); *G16H 40/63* (2018.01); *G16H 50/70* (2018.01); *G16Z 99/00* (2019.02); *A61B 5/684* (2013.01); *A61B 5/743* (2013.01); *A61B 5/748* (2013.01); *A61M 2005/14208* (2013.01); *A61M 2205/502* (2013.01); *A61M 2205/52* (2013.01)

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,755,173 A | 7/1988 | Konopka et al. |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,522,803 A | 6/1996 | Teissen-Simony |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illliff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,807,375 A | 9/1998 | Gross et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Eliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,954,643 A | 9/1999 | Van Antwerp et al. |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |

(56) References Cited

U.S. PATENT DOCUMENTS

| | | |
|---|---|---|
| 5,999,849 A | 12/1999 | Gord et al. |
| 6,009,339 A | 12/1999 | Bentsen et al. |
| 6,017,328 A | 1/2000 | Fischell et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,259,937 B1 | 7/2001 | Schulman et al. |
| 6,329,161 B1 | 12/2001 | Heller et al. |
| 6,355,021 B1 | 3/2002 | Nielsen et al. |
| 6,379,301 B1 | 4/2002 | Worthington et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,544,212 B2 | 4/2003 | Galley et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,591,876 B2 | 7/2003 | Safabash |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,736,797 B1 | 5/2004 | Larsen et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,587 B2 | 6/2004 | Flaherty |
| 6,749,740 B2 | 6/2004 | Liamos et al. |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,153,263 B2 | 12/2006 | Carter et al. |
| 7,153,289 B2 | 12/2006 | Vasko |
| 7,303,549 B2 | 12/2007 | Flaherty et al. |
| 7,323,142 B2 | 1/2008 | Pendo et al. |
| 7,395,330 B2 | 7/2008 | Banet et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV |
| 8,674,288 B2 | 3/2014 | Hanson et al. |
| 10,201,657 B2 | 2/2019 | Parikh et al. |
| 11,027,064 B2 | 6/2021 | Parikh et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |

(56) References Cited

U.S. PATENT DOCUMENTS

| | | |
|---|---|---|
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihal et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0031094 A1 | 2/2006 | Cohen et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0123819 A1 | 5/2007 | Mernoe et al. |
| 2007/0135866 A1 | 6/2007 | Baker et al. |
| 2008/0154503 A1 | 6/2008 | Wittenber et al. |
| 2008/0161664 A1 | 7/2008 | Mastrototaro et al. |
| 2009/0081951 A1 | 3/2009 | Erdmann et al. |
| 2009/0082635 A1 | 3/2009 | Baldus et al. |
| 2009/0240120 A1 | 9/2009 | Mensinger et al. |
| 2010/0160861 A1 | 6/2010 | Causey, III et al. |
| 2010/0185175 A1 | 7/2010 | Kamen et al. |
| 2011/0184268 A1 | 7/2011 | Taub |
| 2013/0338630 A1 | 12/2013 | Agrawal et al. |
| 2015/0057634 A1 | 2/2015 | Mastrototaro et al. |
| 2015/0057807 A1 | 2/2015 | Mastrototaro et al. |
| 2015/0135118 A1 | 5/2015 | Grubstein et al. |
| 2019/0125970 A1 | 5/2019 | Parikh et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 9620745 | 7/1996 |
| WO | WO 9636389 | 11/1996 |
| WO | WO 9637246 A1 | 11/1996 |
| WO | WO 9721456 | 6/1997 |
| WO | WO 9820439 | 5/1998 |
| WO | WO 9824358 | 6/1998 |
| WO | WO 9842407 | 10/1998 |
| WO | WO 9849659 | 11/1998 |
| WO | WO 9859487 | 12/1998 |
| WO | WO 9908183 | 2/1999 |
| WO | WO 9910801 | 3/1999 |
| WO | WO 9918532 | 4/1999 |
| WO | WO 9922236 | 5/1999 |
| WO | WO 0010628 | 3/2000 |
| WO | WO 0019887 | 4/2000 |
| WO | WO 0048112 | 8/2000 |
| WO | WO 02058537 | 8/2002 |
| WO | WO 03001329 | 1/2003 |
| WO | WO 03094090 | 11/2003 |
| WO | WO 2005065538 | 7/2005 |
| WO | 2012170000 A1 | 12/2012 |

OTHER PUBLICATIONS (Animas Corporation, 1999). Animas . . . bringing new life to insulin therapy. (Applicant points out, in accordance with MPEP 609.04(a), that the year of publication, 1999 is sufficiently earlier than the effective U.S. filing date, so that the particular month of publication is not in issue.).

(Intensive Diabetes Management, 1995). Insulin Infusion Pump Therapy. pp. 66-78. (Applicant points out, in accordance with MPEP 609.04(a), that the year of publication, 1995 is sufficiently earlier than the effective U.S. filing date, so that the particular month of publication is not in issue.).

(Medtronic MiniMed, 2002). Medtronic MiniMed Meal Bolus Calculator and Correction Bolus Calculator. International Version. (Applicant points out, in accordance with MPEP 609.04(a), that the year of publication, 2002 is sufficiently earlier than the effective U.S. filing date, so that the particular month of publication is not in issue.).

(Medtronic MiniMed, 2002). The 508 Insulin Pump A Tradition of Excellence. (Applicant points out, in accordance with MPEP 609.04(a), that the year of publication, 2002 is sufficiently earlier than the effective U.S. filing date, so that the particular month of publication is not in issue.).

(Mini Med Inc., 2000). Now [I] Can MiniMed Diabetes Management. (Applicant points out, in accordance with MPEP 609.04(a), that the year of publication, 2000 is sufficiently earlier than the effective U.S. filing date, so that the particular month of publication is not in issue.).

(Mini Med Inc., 2000). Now [I] Can MiniMed Pump Therapy. (Applicant points out, in accordance with MPEP 609.04(a), that the year of publication, 2000 is sufficiently earlier than the effective U.S. filing date, so that the particular month of publication is not in issue.).

(MiniMed Inc., 1999). Insulin Pump Comparison I Pump Therapy Will Change Your Life. (Applicant points out, in accordance with MPEP 609.04(a), that the year of publication, 1999 is sufficiently earlier than the effective U.S. filing date, so that the particular month of publication is not in issue.).

(MiniMed Inc., 1999). MiniMed 508 Flipchart Guide to Insulin Pump Therapy. (Applicant points out, in accordance with MPEP 609.04(a), that the year of publication, 1999 is sufficiently earlier than the effective U.S. filing date, so that the particular month of publication is not in issue.).

(MiniMed Inc., 2000). MiniMed® Now [I] Can Meal Bolus Calculator I MiniMed® Now [I] Can Correction Bolus Calculator. (Applicant points out, in accordance with MPEP 609.04(a), that the year of publication, 2000 is sufficiently earlier than the effective U.S. filing date, so that the particular month of publication is not in issue.).

(MiniMed International, 1998). MiniMed 507C Insulin Pump For those who appreciate the difference. (Applicant points out, in accordance with MPEP 609.04(a), that the year of publication, 1998 is sufficiently earlier than the effective U.S. filing date, so that the particular month of publication is not in issue.).

(MiniMed Technologies, 1994). MiniMed 506 Insulin Pump User's Guide. (Applicant points out, in accordance with MPEP 609.04(a), that the year of publication, 1994 is sufficiently earlier than the effective U.S. filing date, so that the particular month of publication is not in issue.).

(MiniMed Technologies, 1994). MiniMed™ Dosage Calculator Initial Meal Bolus Guidelines / MiniMedTM Dosage Calculator Initial Basal Rate Guidelines Percentage Method. 4 pages. (Applicant points out, in accordance with MPEP 609.04(a), that the year of publication, 1994, is sufficiently earlier than the effective U.S. filing date, so that the particular month of publication is not in issue).

(MiniMed, 1996). FAQ: The Practical Things . . . pp. 1-4. Retrieved on Sep. 16, 2003 from the World Wide Web: http://web.archive.org/web/19961111 054546/www.minimed.com/files/faq_pract.htm.

(MiniMed, 1996). MiniMed™ 507 Insulin Pump User's Guide. (Applicant points out, in accordance with MPEP 609.04(a), that the

(56) References Cited

OTHER PUBLICATIONS year of publication, 1996, is sufficiently earlier than the effective U.S. filing date, so that the particular month of publication is not in issue).
(MiniMed, 1996). The MiniMed 506. 7 pages. Retrieved on Sep. 16, 2003 from the World Wide Web: h!tp://web.archive.org/web/19961111 054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1997). MiniMed™ 507 Insulin Pump User's Guide. (Applicant points out, in accordance with MPEP 609.04(a), that the year of publication, 1997, is sufficiently earlier than the effective U.S. filing date, so that the particular month of publication is not in issue).
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed, 1998). MiniMed 507C Insulin Pump User's Guide. (Applicant points out, in accordance with MPEP 609.04(a), that the year of publication, 1998, is sufficiently earlier than the effective U.S. filing date, so that the particular month of publication is not in issue).
(MiniMed, 2000). MiniMed® 508 User's Guide. (Applicant points out, in accordance with MPEP 609.04(a), that the year of publication, 2000, is sufficiently earlier than the effective U.S. filing date, so that the particular month of publication is not in issue).
Abel et al., "Experience with an implantable glucose sensor as a prerequisite of an artificial beta cell," Biomed. Biochim. Acta 43 (1984) 5, pp. 577-584. (Applicant points out, in accordance with MPEP 609.04(a), that the year of publication, 1984, is sufficiently earlier than the effective U.S. filing date, so that the particular month of publication is not in issue).
Bindra et al., "Design and in Vitro Studies of a Needle-Type Glucose Sensor for a Subcutaneous Monitoring," American Chemist Society, vol. 63, No. 17, Sep. 1991, pp. 1692-1696.
Bode et al., "Reduction in Severe Hypoglycemia with Long-Term Continuous Subcutaneous Insulin Infusion in Type I Diabetes," Diabetes Care, vol. 19, No. 4, Apr. 1996, pp. 324-327.
Boguslavsky et al., "Applications of redox polymers in biosensors," Sold State Ionics, vol. 60, Mar. 1993, pp. 189-197.
Boland E (Jan. 1998). Teens Pumping it Up! Insulin Pump Therapy Guide for Adolescents. 2nd Edition.
Brackenridge B P (1992). Carbohydrate Gram Counting A Key to Accurate Mealtime Boluses in Intensive Diabetes Therapy. Practical Diabetology, vol. 11, No. 2, pp. 22-28. (Applicant points out, in accordance with MPEP 609.04(a), that the year of publication, 1992, is sufficiently earlier than the effective U.S. filing date, so that the particular month of publication is not in issue).
Brackenridge, B P et al. (1995). Counting Carbohydrates How to Zero in on Good Control. MiniMed Technologies Inc. (Applicant points out, in accordance with MPEP 609.04(a), that the year of publication, 1995, is sufficiently earlier than the effective U.S. filing date, so that the particular month of publication is not in issue).
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138. (Applicant points out, in accordance with MPEP 609.04(a), that the year of publication, 1994, is sufficiently earlier than the effective U.S. filing date, so that the particular month of publication is not in issue).
Geise et al., "Electropolymerized 1 ,3-diaminobenzene for the construction of a 1,1'-dimethylferrocene mediated glucose biosensor," Analytica Chimica Acta, vol. 281, No. 3, Sep. 1993, pp. 467-473.
Gernet et al., "A Planar Glucose Enzyme Electrode," Sensors and Actuators, vol. 17, May 1989, pp. 537-540.
Gernet et al., "Fabrication and Characterization of a Planar Electromechanical Cell and its Application as a Glucose Sensor," Sensors and Actuators, vol. 18, Jun. 1989, pp. 59-70.

Gorton et al., "Amperometric Biosensors Based on an Apparent Direct Electron Transfer Between Electrodes and Immobilized Peroxdiases," Analyst, Aug. 1991, vol. 117, pp. 1235-1241.
Gorton, L., et al., "Amperometric Glucose Sensors Based on Immobilized Glucose-Oxidizing Enzymes and Chemically Modified Electrodes," Analytica Chimica Acta, vol. 249, 1991, pp. 43-54. (Applicant points out, in accordance with MPEP 609.04(a), that the year of publication, 1991, is sufficiently earlier than the effective U.S. filing date, so that the particular month of publication is not in issue).
Gough et al., "Two-Dimensional Enzyme Electrode Sensor for Glucose," Analytical Chemistry, vol. 57, No. 12, Oct. 1985, pp. 2351-2357.
Gregg, Brian A., et al., "Cross-Linked Redox Gels Containing Glucose Oxidase for Amperometric Biosensor Applications," Analytical Chemistry, vol. 62, No. 3, Feb. 1990, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, Jul. 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Ace. Chem. Res., vol. 23, No. 5, May 1990, pp. 128-134.
Hirsch et al., "Intensive Insulin Therapy for Treatment of Type I Diabetes," Diabetes Care, vol. 13, No. 12, Dec. 1990, pp. 1265-1283.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, Sep. 1992, pp. 709-714.
Jonsson, G., et al., "An Electromechanical Sensor for Hydrogen Peroxide Based on Peroxidase Adsorbed on a Spectrographic Graphite Electrode," Electroanalysis, vol. 1, No. 5, Sep. 1989, pp. 465-468.
Kanapieniene, J. J., et al., "Miniature Glucose Biosensor with Extended Linearity," Sensors and Actuators, B: Chemical, vol. 10, No. 1, Dec. 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
D. Barry Keenan, Ph.D., et al., "Delays in Minimally Invasive Continuous Minotoring Devices: A Review of Current Technology," Journal of Diabetes Science and Technology, vol. 3, Issue 5, Sep. 2009, pp. 1207-1214, Diabetes Technology Society.
Desmond Barry Keenan, Ph.D., et al., "Accuracy of the Enlite 6-Day Glucose Sensor with Guardian and Veo Calibration Algorithms," Diabetes Technology & Therapeutics, vol. 14, No. 3, 2012, pp. 1-7, Mary Ann Liebert, Inc.
Kimura, J., et al., "An Immobilized Enzyme Membrane Fabrication Method," Biosensors, vol. 4, No. 1, May 18, 1988, pp. 41-52.
Koudelka, M., et al., "In-vivo Behaviour of Hypodermically Implanted Microfabricated Glucose Sensors," Biosensors & Bioelectronics, vol. 6, May 1, 1991, pp. 31-36.
Koudelka, M., et al., "Planar Amperometric Enzyme-Based Glucose Microelectrode," Sensors & Actuators, vol. 18, Jun. 1989, pp. 157-165.
Kulkarni K et al. (Jan. 1999). Carbohydrate Counting A Primer for Insulin Pump Users to Zero in on Good Control. MiniMed Inc.
Marcus et al., "Insulin Pump Therapy Acceptable Alternative to Injection Therapy," Postgraduate Medicine, vol. 99, No. 3, Mar. 1996, pp. 125-142.
Mastrototaro et al., "An electroenzymatic glucose sensor fabricated on a flexible substrate," Sensors & Actuators, B: Chemical; vol. 5, Aug. 1991, pp. 139-144.

(56) References Cited

OTHER PUBLICATIONS

Mastrototaro et al., "An Electroenzymatic Sensor Capable of 72 Hour Continuous Monitoring of Subcutaneous Glucose," 14th Annual International Diabetes Federation Congress, Washington D.C., Jun. 23-28, 1991.
Mckean, Brian D., et al., "A Telemetry-Instrumentation System for Chronically Implanted Glucose and Oxygen Sensors," IEEE Transactions on Biomedical Engineering, vol. 35, No. 7, Jul. 1988, pp. 526-532.
Michael S. Boyne, et al., "Timing of Changes in Interstitial and Venous Blood Glucose Measured With a Continuous Subcutaneous Glucose Sensor," Diabetes, 2003, vol. 52, pp. 2790-2794. (Applicant points out, in accordance with MPEP 609.04(a), that the year of publication, 2003, is sufficiently earlier than the effective U.S. filing date, so that the particular month of publication is not in issue.).
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annual International Conference of the IEEE Engineering in Medicine and Biology Society, vol. 12, No. 2, Nov. 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators, vol. 13, Feb. 1988, pp. 165-172.
Nishida, Kenro, et al., "Clinical applications of the wearable artificial endocrine pancreas with the newly designed needle-type glucose sensor," Elsevier Sciences B.V., 1994, pp. 353-358. (Applicant points out, in accordance with MPEP 609.04(a), that the year of publication, 1994, is sufficiently earlier than the effective U.S. filing date, so that the particular month of publication is not in issue).
Nishida, Kenro, et al., "Development of a ferrocene-mediated needle-type glucose sensor covered with newly designed biocompatible membrane, 2-methacryloyloxyethyl phosphorylcholine-co-n-butyl methacrylate," Medical Progress Through Technology, vol. 21, Apr. 1995, pp. 91-103.
Poitout, V., et al., "A glucose monitoring system for on line estimation in man of blood glucose concentration using a miniaturized glucose sensor implanted in the subcutaneous tissue and a wearable control unit," Diabetologia, vol. 36, Jul. 1991, pp. 658-663.
Reach, G., "A Method for Evaluating in vivo the Functional Characteristics of Glucose Sensors," Biosensors, vol. 2, Jul. 7, 1986, pp. 211-220.
Kerstin Rebrin, et al., Can Interstitial Glucose Assessment Replace Blood Glucose Measurements? Diabetes Technology & Therapeutics, vol. 2, No. 3, 2000, pp. 461-472. (Applicant points out, in accordance with MPEP 609.04(a), that the year of publication, 2000, is sufficiently earlier than the effective U.S. filing date, so that the particular month of publication is not in issue).
Reed, J., "Living with Diabetes," Voice of the Diabetic, vol. 11, No. 3, Summer Edition 1996, pp. 1-38. (Applicant points out, in accordance with MPEP 609.04(a), that the year of publication, 1996, is sufficiently earlier than the effective U.S. filing date, so that the particular month of publication is not in issue).
Sara Wilson Reece, "Insulin Pump Class: Back to the Basics of Pump Therapy," Diabetes Spectrum, vol. 27, No. 2, 2014, pp. 135-140. (Applicant points out, in accordance with MPEP 609.04(a), that the year of publication, 2014, is sufficiently earlier than the effective U.S. filing date, so that the particular month of publication is not in issue).
Gary Scheiner, et al, "Insulin Pump Therapy: Guidelines for Successful Outcomes," American Association of Diabetes Educators 2008, Consensus Summit, Sep. 18, 2008, Chicago, IL.

Shaw, G. W., et al., "In vitro testing of a simply constructed, highly stable glucose sensor suitable for implantation in diabetic patients," Biosensors & Bioelectronics, vol. 6, Oct. 1991, pp. 401-406.
Shichiri, M., "A Needle-Type Glucose Sensor—A Valuable Tool Not Only for a Self-Blood Glucose Monitoring but for a Wearable Artificial Pancreas," Life Support Systems Proceedings, XI Annual Meeting ESAO, Alpbach-Innsbruck, Austria, Sep. 1984, pp. 7-9.
Shichiri, M., et al., "In Vivo Characteristics of Needle-Type Glucose Senso—Measurements of Subcutaneous Glucose Concentrations in Human Volunteers," Hormone and Metabolic Research, Supplement Series vol. No. 20, 1988, pp. 17-20. (Applicant points out, in accordance with MPEP 609.04(a), that the year of publication, 1988, is sufficiently earlier than the effective U.S. filing date, so that the particular month of publication is not in issue).
Shichiri, M., et al., "Membrane design for extending the long-life of an implantable glucose sensor," Diab. Nutr. Metab., vol. 2, No. 4, 1989, pp. 309-313. (Applicant points out, in accordance with MPEP 609.04(a), that the year of publication, 1989, is sufficiently earlier than the effective U.S. filing date, so that the particular month of publication is not in issue).
Shichiri, Motoaki, et al., "An artificial endocrine pancreas—problems awaiting solution for long-term clinical applications of a glucose sensor," Frontiers Med. Bioi. Engng., 1991, vol. 3, No. 4, pp. 283-292. (Applicant points out, in accordance with MPEP 609.04(a), that the year of publication, 1991, is sufficiently earlier than the effective U.S. filing date, so that the particular month of publication is not in issue).
Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.
Shichiri, Motoaki, et al., "Glycaemic Control in a Pancreatectomized Dogs with a Wearable Artificial Endocrine Pancreas," Diabetologia, vol. 24, Mar. 1983, pp. 179-184.
Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.
Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.
Shichiri, Motoaki, et al., "The Wearable Artificial Endocrine Pancreas with a Needle-Type Glucose Sensor: Perfect Glycemic Control in Ambulatory Diabetes," Acta Paediatr Jpn, Sep. 1984, vol. 26, pp. 359-370.
Shichiri, Motoaki, et al., "Wearable Artificial Endocrine Pancreas with Needle-Type Glucose Sensor," The Lancet, Nov. 20, 1982, pp. 1129-1131.
Shinkai, Seiji, "Molecular Recognition of Mono- and Di-saccharides by Phenylboronic Acids in Solvent Extraction and as a Monolayer," J. Chem. Soc., Chem. Commun., vol. 15, Aug. 1991, pp. 1039-1041.
Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.
Skyler J S (1989). Continuous Subcutaneous Insulin Infusion [CSII] With External Devices: Current Status. Update in Drug Delivery Systems, Chapter 13, pp. 163-183. Futura Publishing Company. (Applicant points out, in accordance with MPEP 609.04(a), that the year of publication, 1989, is sufficiently earlier than the effective U.S. filing date, so that the particular month of publication is not in issue).
Skyler J S et al. (1995). The Insulin Pump Therapy Book Insights from the Experts. MiniMed•Technologies. (Applicant points out, in accordance with MPEP 609.04(a), that the year of publication, 1995, is sufficiently earlier than the effective U.S. filing date, so that the particular month of publication is not in issue).
Sternberg, Robert, et al., "Study and Development of Multilayer Needle-type Enzyme-based Glucose Microsensors," Biosensors, vol. 4, Dec. 1988, pp. 27-40.
Strowig S M, "Initiation and Management of Insulin Pump Therapy," The Diabetes Educator, vol. 19, No. 1, Feb. 1993, pp. 50-60.

(56) References Cited

OTHER PUBLICATIONS

Tamiya, E., et al., "Micro Glucose Sensors using Electron Mediators Immobilized on a Polypyrrole-Modified Electrode," Sensors and Actuators, vol. 18, Jul. 1989, pp. 297-307.

Tsukagoshi, Kazuhiko, et al., "Specific Complexation with Mono- and Disaccharides that can be Detected by Circular Dichroism," J. Org. Chem., vol. 56, Jun. 1991, pp. 4089-4091.

Ubran, G., et al., "Miniaturized thin-film biosensors using covalently immobilized glucose oxidase," Biosensors & Bioelectronics, vol. 6, Jan. 1991, pp. 555-562.

Urban, G., et al., "Miniaturized multi-enzyme biosensors integrated with pH sensors on flexible polymer carriers for in vivo applications," Biosensors & Bioelectronics, vol. 7, Sep. 1992, pp. 733-739.

Velho, G., et al., "In vivo calibration of a subcutaneous glucose sensor for determination of subcutaneous glucose kinetics," Diab. Nutr. Metab., vol. 3, 1988, pp. 227-233. (Applicant points out, in accordance with MPEP 609.04(a), that the year of publication, 1988, is sufficiently earlier than the effective U.S. filing date, so that the particular month of publication is not in issue).

Walsh J, et al. (1989). Pumping Insulin: The Art of Using an Insulin Pump. Published by MiniMed•Technologies. (Applicant points out, in accordance with MPEP 609.04(a), that the year of publication, 1989, is sufficiently earlier than the effective U.S. filing date, so that the particular month of publication is not in issue).

Wang, Joseph, et al., "Needle-Type Dual Microsensor for the Simultaneous Monitoring of Glucose and Insulin," Analytical Chemistry, vol. 73, Feb. 2001, pp. 844-847.

Howard Wolpert, "Establishing a Continuous Glucose Monitoring Program," Journal of Diabetes Science and Technology, vol. 2, Mar. 2008, pp. 307-310.

Howard Wolpert, "Use of Continuous Glucose Monitoring in the Detection and Prevention of Hypoglycemia," Journal of Diabetes Science and Technology, vol. 1, Issue 1, Jan. 2007, pp. 146-150.

Yamasaki, Yoshimitsu, et al., "Direct Measurement of Whole Blood Glucose by a Needle-Type Sensor," Clinics Chimica Acta, vol. 180, Mar. 1989, pp. 93-98.

Yokoyama, K., "Integrated Biosensor for Glucose and Galactose," Analytica Chimica Acta, vol. 218, 1989, pp. 137-142. (Applicant points out, in accordance with MPEP 609.04(a), that the year of publication, 1989, is sufficiently earlier than the effective U.S. filing date, so that the particular month of publication is not in issue).

Prosecution History from U.S. Appl. No. 15/240,720, dated Jan. 26, 2018 through Sep. 25, 2018, 39 pp.

Prosecution History from U.S. Appl. No. 16/224,697, dated Aug. 24, 2020 through Feb. 1, 2021, 14 pp.

Examiner's Requisition from counterpart Canadian Application No. 2994726 dated November 15, 2022, 3 pp.

Response to Extended Search Report dated May 24, 2022, from counterpart European Application No. 22156002.2, filed Dec. 22, 2022, 16 pp.

Extended Search Report from counterpart European Application No. 22156002.2 dated May 24, 2022, 9 pp.

International Preliminary Report on Patentability dated Mar. 8, 2018 in Application No. PCT/US2016/047878.

International Search Report and Written Opinion dated Nov. 23, 2016 in PCT Application No. PCT/US2016/047878.

U.S. Non-Final Office Action dated Aug. 24, 2020, in U.S. Appl. No. 16/224,697.

U.S. Non-Final Office Action dated May 11, 2018, in U.S. Appl. No. 15/240,720.

U.S. Notice of Allowance dated Feb. 1, 2021 in U.S. Appl. No. 16/224,697.

U.S. Notice of Allowance dated Sep. 25, 2018 in U.S. Appl. No. 15/240,720.

U.S. Restriction Requirement dated Jan. 26, 2018 in U.S. Appl. No. 15/240,720.

IDENTIFICATION OF SITES FOR SENSING ARRANGEMENTS

CROSS-REFERENCE TO RELATED APPLICATION(S)

This application is a continuation of U.S. patent application Ser. No. 16/224,697, filed Dec. 18, 2018, which is a continuation of U.S. patent application Ser. No. 15/240,720, filed Aug. 18, 2016, which claims the benefit of U.S. Provisional Patent Application Ser. No. 62/208,486, filed Aug. 21, 2015, the entire contents of each of which is incorporated by reference herein.

TECHNICAL FIELD

Embodiments of the subject matter described herein relate generally to medical devices, and more particularly, embodiments of the subject matter relate to mitigating effects of sensor lag during operation of a fluid infusion device.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Continuous insulin infusion provides greater control of a patient with diabetes glucose levels, and hence, control schemes are being developed that allow insulin infusion pumps to monitor and regulate a user's blood glucose level in a substantially continuous and autonomous manner. Regulating blood glucose level is complicated by variations in the response time for the type of insulin being used along with variations in a user's individual insulin response and daily activities (e.g., exercise, carbohydrate consumption, bolus administration, and the like). Additionally, the responsiveness of the glycemic control can be influenced by delay associated with feedback regarding the user's current glucose level.

For example, some continuous glucose monitoring (CGM) sensors measure the glucose in the interstitial fluid (ISF) while blood glucose meters used for calibration measure the blood glucose in the capillaries. Blood glucose diffuses from the capillary to the interstitial space where it is measured by the CGM sensor, which results in ISF glucose measurements lagging behind the blood glucose measurements based on the time it takes glucose to diffuse from the capillary to the interstitial space. In addition to the physiological time lag, signal processing (e.g., filtering), signal interference (e.g., noise), and sensor characteristics may also influence the amount by which the ISF glucose measurements lag the blood glucose in the capillaries. Accordingly, there is a need to mitigate the effects of sensor lag and improve the responsiveness and efficacy of glycemic control.

BRIEF SUMMARY

Infusion systems, infusion devices, sensing devices, and related operating methods are provided. In one example, the disclosure describes a processor-implemented method that includes obtaining measurement data indicative of a physiological condition measured by a sensing arrangement located at a site on a body, determining a lag associated with the sensing arrangement based on a relationship between the measurement data and reference data, and identifying, based on the lag, the site at which the sensing arrangement is located from a plurality of sites on the body.

In one example, the disclosure describes a system comprising one or more processors and one or more processor-readable storage media storing instructions which, when executed by the one or more processors, cause performance of obtaining measurement data indicative of a physiological condition measured by a sensing arrangement located at a site on a body, determining a lag associated with the sensing arrangement based on a relationship between the measurement data and reference data, and identifying, based on the lag, the site at which the sensing arrangement is located from a plurality of sites on the body.

In one example, the disclosure describes one or more non-transitory processor-readable storage media storing instructions which, when executed by one or more processors, cause performance of obtaining measurement data indicative of a physiological condition measured by a sensing arrangement located at a site on a body, determining a lag associated with the sensing arrangement based on a relationship between the measurement data and reference data, and identifying, based on the lag, the site at which the sensing arrangement is located from a plurality of sites on the body.

An embodiment of a method of operating an infusion device to deliver fluid capable of influencing a physiological condition to a body of a user is provided. The method involves identifying a current site location on the body of the user associated with a sensing arrangement providing sensed measurements of a physiological condition in the body of the user at the current site location, determining one or more performance metrics associated with the current site location corresponding to operation of the infusion device to deliver the fluid in response to the sensed measurements, and providing sensor site feedback in a manner that is influenced by the one or more performance metrics.

In another embodiment, an infusion system is provided that includes a sensing arrangement to obtain measurement values for a physiological condition from a body of a user and an infusion device. The infusion device includes an actuation arrangement operable to deliver fluid influencing the physiological condition to the body of the user, a user interface, and a control system coupled to the actuation arrangement and the sensing arrangement. The control system is configured to autonomously operate the actuation arrangement to deliver the fluid based on the measurement values, identify a current site location on the body of the user associated with the sensing arrangement, determine one or more performance metrics associated with the current site location based on the measurement values, and provide sensor site feedback via the user interface in a manner that is influenced by the one or more performance metrics.

In another embodiment, a system is provided that includes a sensing arrangement to obtain measurement values for a physiological condition from a body of a user, an infusion device communicatively coupled to the sensing arrangement and including an actuation arrangement operable to deliver fluid influencing the physiological condition to the body of the user in response to the measurement values, a database to maintain historical data associated with the user, and a server coupled to the database and a network. The server is configured to identify a current site location on the body of the user associated with the sensing arrangement based on one or more of the measurement values and the historical data, determine one or more performance metrics associated with the current site location based on the measurement values associated with autonomous operation of the infusion device to deliver the fluid, and provide site rotation feedback in a manner that is influenced by the one or more performance metrics and the historical data.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
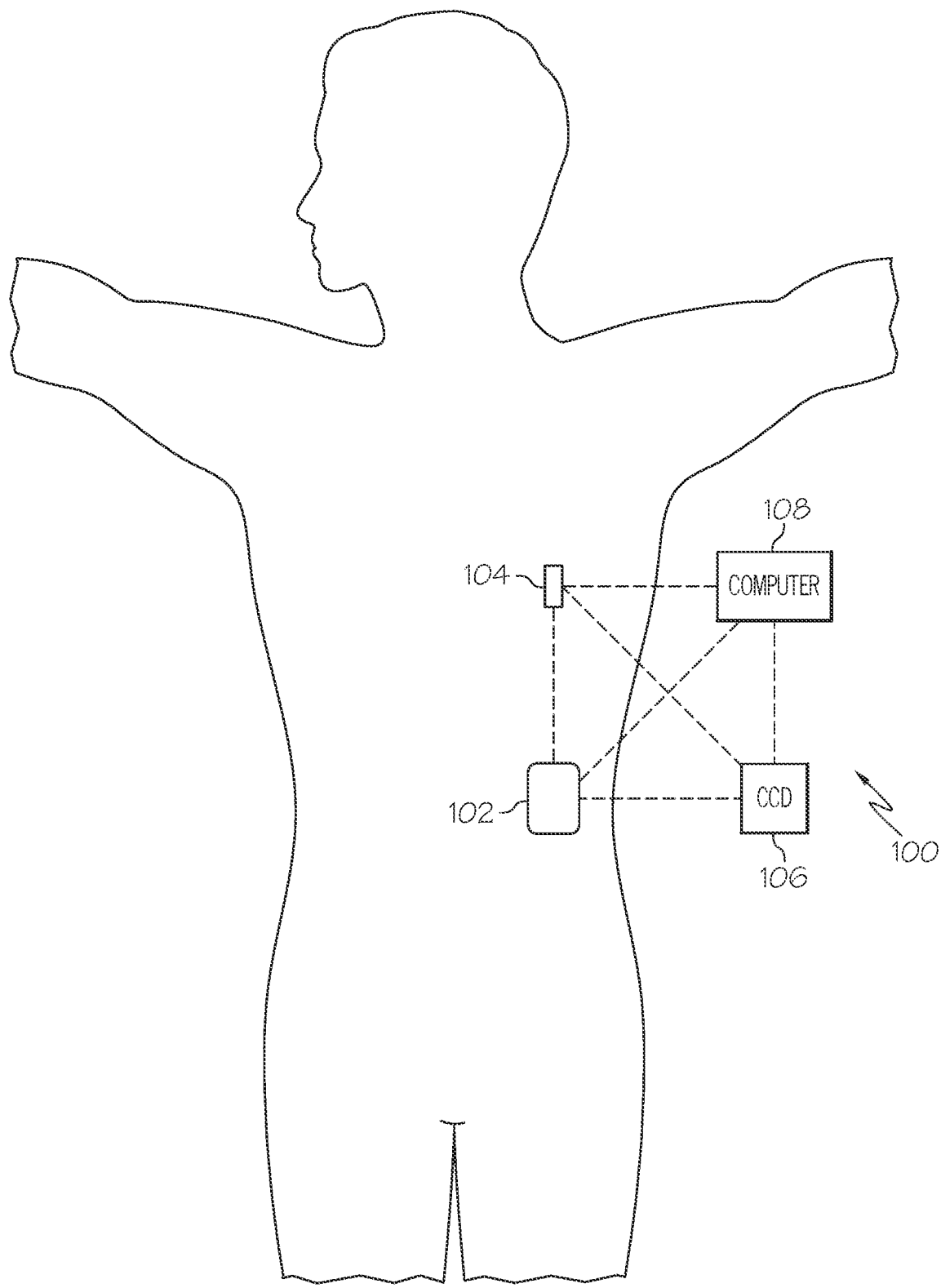
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to infusion systems including a fluid infusion device having a motor that is operable to linearly displace a plunger (or stopper) of a reservoir provided within the fluid infusion device to deliver a dosage of fluid, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

As described in greater detail below, primarily in the context of FIGS. 8-11, in exemplary embodiments described herein, the current location on the body of a patient where a sensing arrangement is attached, inserted, or otherwise affixed is identified and utilized to improve the efficacy of regulating a physiological condition in the body of the patient. In this regard, a sensing arrangement may be capable of use at a number of different regions of the body, such as, for example, the abdomen, arm, leg, buttocks, or the like. As used herein, a sensor site (or site) should be understood as referring to a distinct region of the body where a sensing arrangement may be attached, inserted, affixed, or otherwise located. It should be noted that different sites may be associated with a common part of the body (e.g., the abdomen) while being physically distinguishable (e.g., different sides of the body, different quadrants or sectors of a body part, or the like).

Based on the site currently associated with the sensing arrangement, sensor site feedback may be provided to the user regarding the current performance or effectiveness of the site and/or whether the site should continue to be used. For example, due to trauma associated with use of the sensing arrangement, it may be desirable to vary or rotate sensing arrangements across different sites to allow tissue of a respective site to heal prior to reuse. In this regard, one or more performance metrics associated with a current sensor site may be calculated or otherwise determined based on the sensor glucose measurements, insulin delivery data, or the like, and based on the value of performance metric(s), a recommendation or indication of whether to rotate the sensor site may be provided.

Additionally, in some embodiments, historical site location information and corresponding measurement and delivery data associated with preceding site locations may be utilized to identify recommended sensor site locations for subsequent site rotations. For example, based on the performance associated with other site locations and the duration of time since they were utilized, one or more recommended sensor site locations deemed most likely to be effective may be identified and one or more corresponding graphical user interface notifications indicating the recommended sensor site location(s) may be provided. Thus, when the user moves, changes or replaces the sensing arrangement, he or she may insert or implant the sensing arrangement at a site on the body that is likely to provide the best glycemic control. The sensor site recommendations may also account for user activity, meal consumption, or other contextual information. For example, the user may input or provide information regarding anticipated exercise, stress, meals, or the like, which, in turn may be utilized to identify a recommended sensor site location likely to provide the best glycemic control given that anticipated delivery context based on a correlation between that site's historical measurement and delivery data for the anticipated delivery context and historical performance metrics associated with the site.

Additionally, in some embodiments, the site currently associated with the sensing arrangement may be utilized to adjust or modify one or more control parameters associated with the autonomous operation of the infusion device to influence delivery of the fluid in a manner that is influenced by the current site location. For example, the calibration factor used to convert an electrical output signal from the sensing arrangement into a corresponding measurement value may be adjusted to account for the lag associated with the current sensor site. In this regard, the calibration factor for a sensor site location having an associated lag of 5 minutes may be determined based on a sensed glucose measurement (or an interpolated glucose measurement) corresponding to 5 minutes after obtaining a reference blood glucose measurement, while the calibration factor for a sensor site location having an associated lag of 15 minutes may be determined based on a sensed glucose measurement (or an interpolated glucose measurement) corresponding to 15 minutes after obtaining a reference blood glucose measurement. Thus, in response to detecting the current sensor site, the calibration factor may be dynamically updated to reflect the current sensor site. Additionally, in some embodiments, based on the amount of lag and/or other performance metrics associated with a sensor site, one or more other control parameters may be adjusted, for example, to increase or decrease responsiveness of a closed-loop control system, to increase or decrease alert thresholds (and thereby influence alerting frequency), or the like.

Infusion System Overview

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological or physiological condition of the user, such as a blood glucose level, or the like, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In various embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In one or more exemplary embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
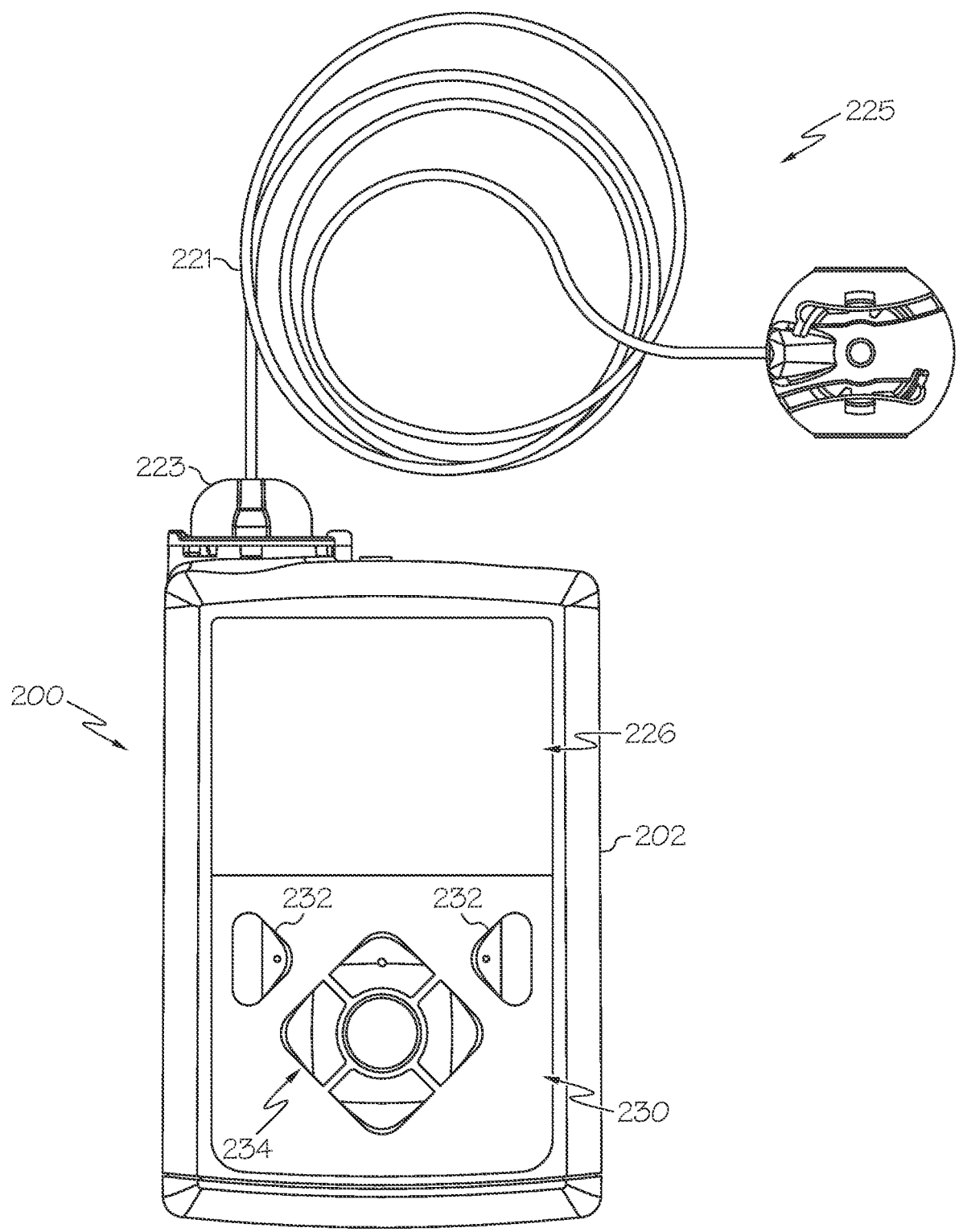
FIG. 2 depicts a plan view of an exemplary embodiment of a fluid infusion device suitable for use in the infusion system of FIG. 1.
Figure 3:
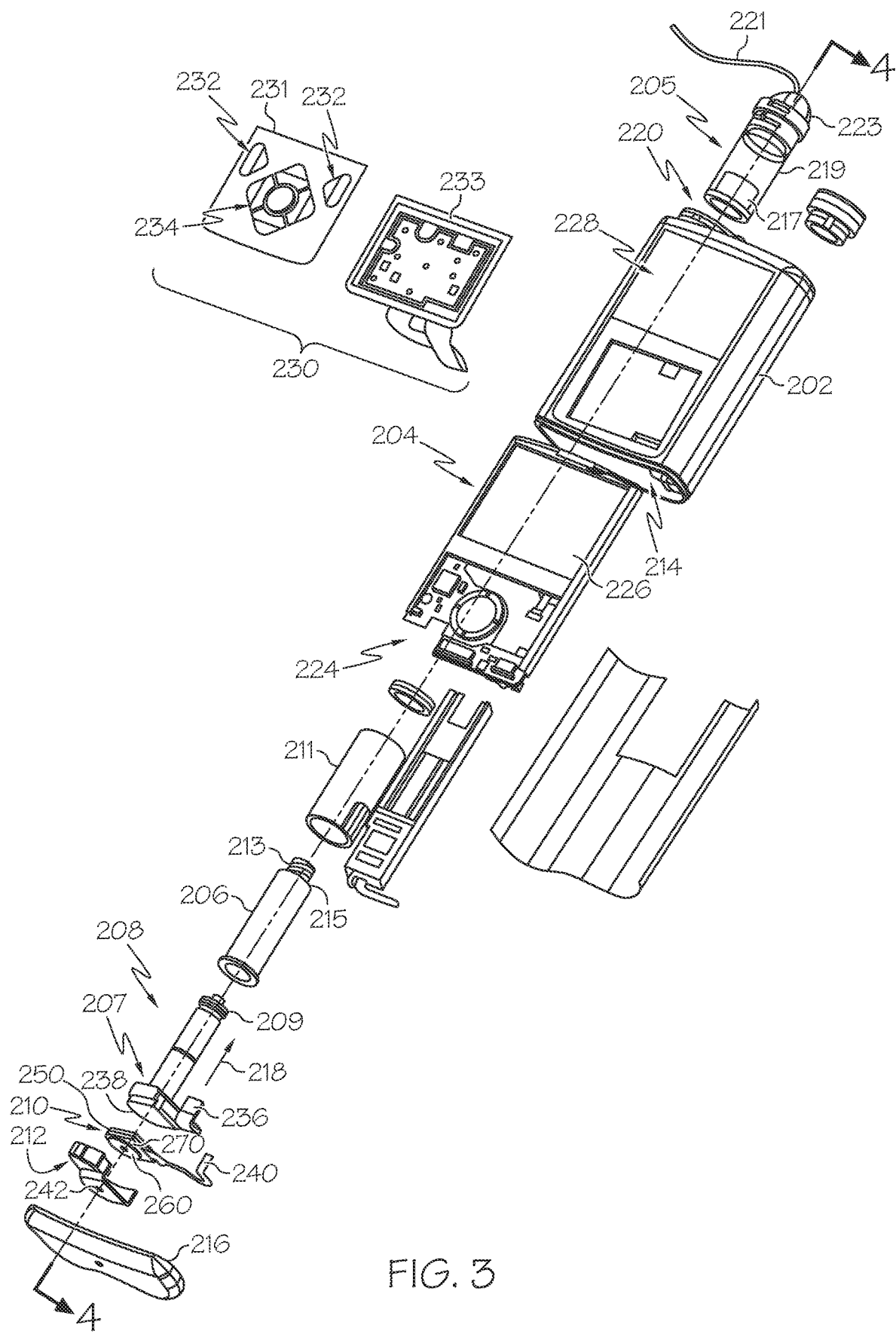
FIG. 3 is an exploded perspective view of the fluid infusion device of FIG. 2.
Figure 4:
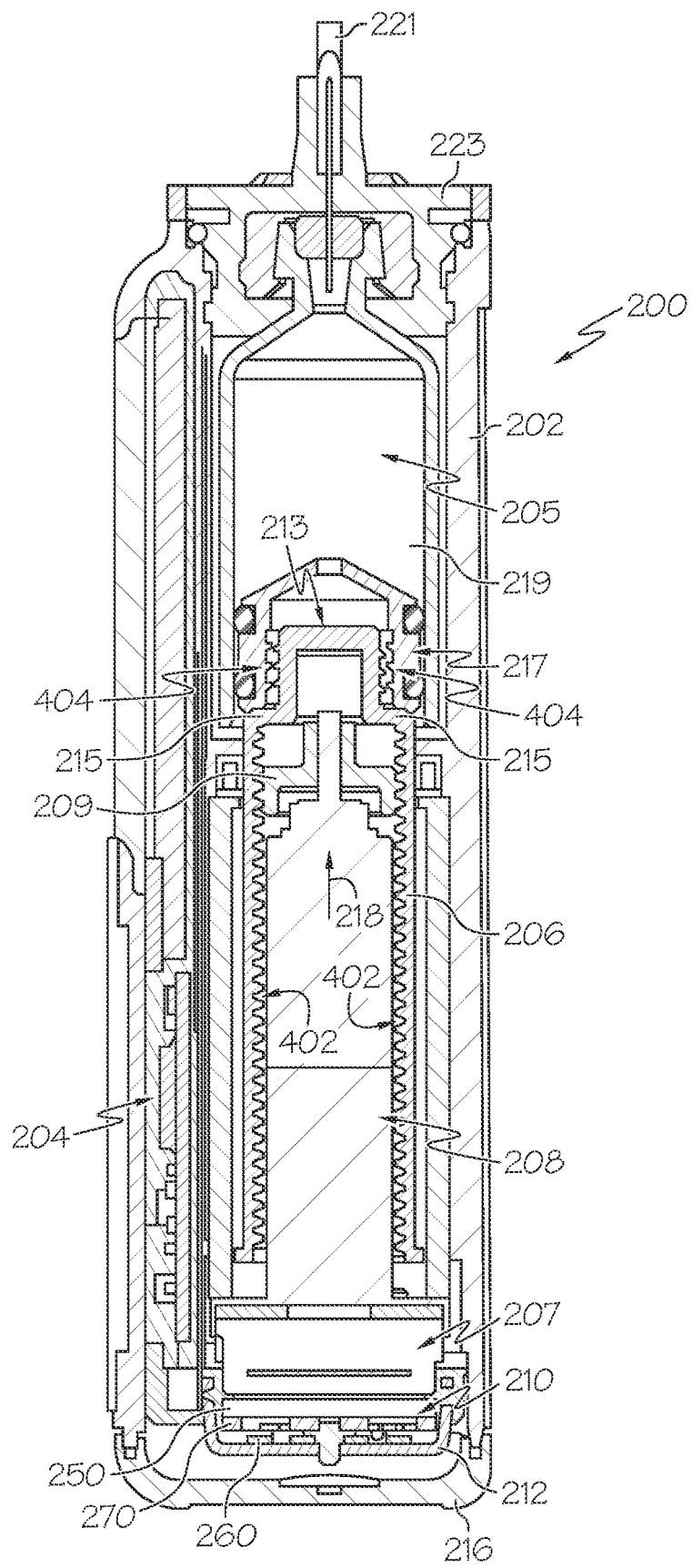
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like.

In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
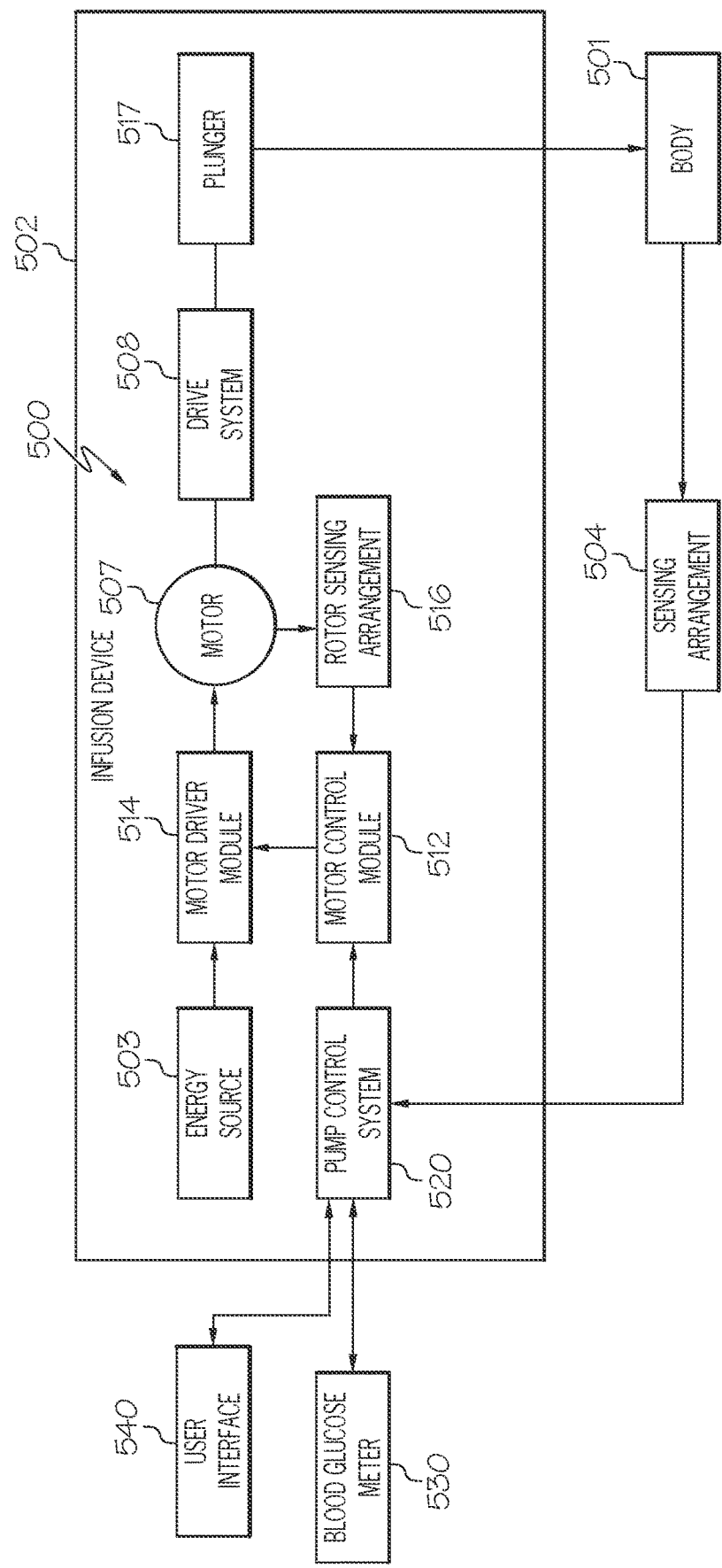
FIG. 5 is a block diagram of an exemplary control system suitable for use in a fluid infusion device, such as the fluid infusion device of FIG. 1 or FIG. 2.

FIG. 5 depicts an exemplary embodiment of a control system 500 suitable for use with an infusion device 502, such as the infusion device 102 in FIG. 1 or the infusion device 200 of FIG. 2. The control system 500 is capable of controlling or otherwise regulating a physiological condition in the body 501 of a user to a desired (or target) value or otherwise maintain the condition within a range of acceptable values in an automated or autonomous manner. In one or more exemplary embodiments, the condition being regulated is sensed, detected, measured or otherwise quantified by a sensing arrangement 504 (e.g., sensing arrangement 104) communicatively coupled to the infusion device 502. However, it should be noted that in alternative embodiments, the condition being regulated by the control system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the user's glucose level, which is being regulated in the body 501 of the user by the control system 500.

In exemplary embodiments, the sensing arrangement 504 includes one or more interstitial glucose sensing elements that generate or otherwise output electrical signals having a signal characteristic that is correlative to, influenced by, or otherwise indicative of the relative interstitial fluid glucose level in the body 501 of the user. The output electrical signals are filtered or otherwise processed to obtain a measurement value indicative of the user's interstitial fluid glucose level. In exemplary embodiments, a blood glucose meter 530, such as a finger stick device, is utilized to directly sense, detect, measure or otherwise quantify the blood glucose in the body 501 of the user. In this regard, the blood glucose meter 530 outputs or otherwise provides a measured blood glucose value that may be utilized as a reference measurement for calibrating the sensing arrangement 504 and converting a measurement value indicative of the user's interstitial fluid glucose level into a corresponding calibrated blood glucose value. For purposes of explanation, the calibrated blood glucose value calculated based on the electrical signals output by the sensing element(s) of the sensing arrangement 504 may alternatively be referred to herein as the sensor glucose value, the sensed glucose value, or variants thereof.

In the illustrated embodiment, the pump control system 520 generally represents the electronics and other components of the infusion device 502 that control operation of the fluid infusion device 502 according to a desired infusion delivery program in a manner that is influenced by the sensed glucose value indicative of a current glucose level in the body 501 of the user. For example, to support a closed-loop operating mode, the pump control system 520 maintains, receives, or otherwise obtains a target or commanded glucose value, and automatically generates or otherwise determines dosage commands for operating an actuation arrangement, such as a motor 507, to displace the plunger 517 and deliver insulin to the body 501 of the user based on the difference between a sensed glucose value and the target glucose value. In other operating modes, the pump control system 520 may generate or otherwise determine dosage commands configured to maintain the sensed glucose value below an upper glucose limit, above a lower glucose limit, or otherwise within a desired range of glucose values. In practice, the infusion device 502 may store or otherwise maintain the target value, upper and/or lower glucose limit(s), and/or other glucose threshold value(s) in a data storage element accessible to the pump control system 520.

The target glucose value and other threshold glucose values may be received from an external component (e.g., CCD 106 and/or computing device 108) or be input by a user via a user interface element 540 associated with the infusion device 502. In practice, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 540 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 5 depicts the user interface element(s) 540 as being separate from the infusion device 502, in practice, one or more of the user interface element(s) 540 may be integrated with the infusion device 502. Furthermore, in some embodiments, one or more user interface element(s) 540 are integrated with the sensing arrangement 504 in addition to and/or in alternative to the user interface element(s) 540 integrated with the infusion device 502. The user interface element(s) 540 may be manipulated by the user to operate the infusion device 502 to deliver correction boluses, adjust target and/or threshold values, modify the delivery control scheme or operating mode, and the like, as desired.

Still referring to FIG. 5, in the illustrated embodiment, the infusion device 502 includes a motor control module 512 coupled to a motor 507 (e.g., motor assembly 207) that is operable to displace a plunger 517 (e.g., plunger 217) in a reservoir (e.g., reservoir 205) and provide a desired amount of fluid to the body 501 of a user. In this regard, displacement of the plunger 517 results in the delivery of a fluid that is capable of influencing the condition in the body 501 of the user to the body 501 of the user via a fluid delivery path (e.g., via tubing 221 of an infusion set 225). A motor driver module 514 is coupled between an energy source 503 and the motor 507. The motor control module 512 is coupled to the motor driver module 514, and the motor control module 512 generates or otherwise provides command signals that operate the motor driver module 514 to provide current (or power) from the energy source 503 to the motor 507 to displace the plunger 517 in response to receiving, from a pump control system 520, a dosage command indicative of the desired amount of fluid to be delivered.

In exemplary embodiments, the energy source 503 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 503 into alternating electrical signals applied to respective phases of the stator windings of the motor 507 that result in current flowing through the stator windings that generates a stator magnetic field and causes the rotor of the motor 507 to rotate. The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 507 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 507 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 507 to achieve the desired delivery of fluid to the user.

When the motor control module 512 is operating the motor driver module 514, current flows from the energy source 503 through the stator windings of the motor 507 to produce a stator magnetic field that interacts with the rotor magnetic field. In some embodiments, after the motor control module 512 operates the motor driver module 514 and/or motor 507 to achieve the commanded dosage, the motor control module 512 ceases operating the motor driver module 514 and/or motor 507 until a subsequent dosage command is received. In this regard, the motor driver module 514 and the motor 507 enter an idle state during which the motor driver module 514 effectively disconnects or isolates the stator windings of the motor 507 from the energy source 503. In other words, current does not flow from the energy source 503 through the stator windings of the motor 507 when the motor 507 is idle, and thus, the motor 507 does not consume power from the energy source 503 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform or otherwise support the tasks, operations, functions, and processes described herein.

It should be appreciated that FIG. 5 is a simplified representation of the infusion device 502 for purposes of explanation and is not intended to limit the subject matter described herein in any way. In this regard, depending on the embodiment, some features and/or functionality of the sensing arrangement 504 may implemented by or otherwise integrated into the pump control system 520, or vice versa. Similarly, in practice, the features and/or functionality of the motor control module 512 may implemented by or otherwise integrated into the pump control system 520, or vice versa. Furthermore, the features and/or functionality of the pump control system 520 may be implemented by control electronics 224 located in the fluid infusion device 200, 400, while in alternative embodiments, the pump control system 520 may be implemented by a remote computing device that is physically distinct and/or separate from the infusion device 502, such as, for example, the CCD 106 or the computing device 108.

Figure 6:
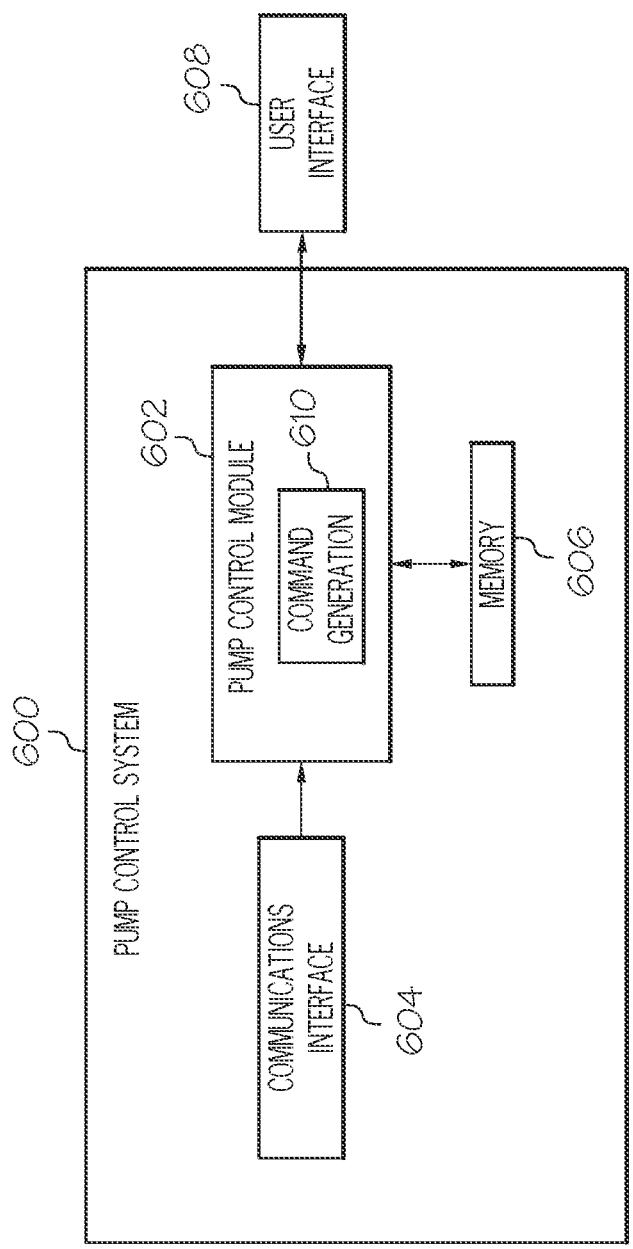
FIG. 6 is a block diagram of an exemplary pump control system suitable for use in the control system of FIG. 5.

FIG. 6 depicts an exemplary embodiment of a pump control system 600 suitable for use as the pump control system 520 in FIG. 5 in accordance with one or more embodiments. The illustrated pump control system 600 includes, without limitation, a pump control module 602, a communications interface 604, and a data storage element (or memory) 606. The pump control module 602 is coupled to the communications interface 604 and the memory 606, and the pump control module 602 is suitably configured to support the operations, tasks, and/or processes described herein. In exemplary embodiments, the pump control module 602 is also coupled to one or more user interface elements 608 (e.g., user interface 230, 540) for receiving user input and providing notifications, alerts, or other therapy information to the user. Although FIG. 6 depicts the user interface element 608 as being separate from the pump control system 600, in various alternative embodiments, the user interface element 608 may be integrated with the pump control system 600 (e.g., as part of the infusion device 200, 502), the sensing arrangement 504 or another element of an infusion system 100 (e.g., the computer 108 or CCD 106).

Referring to FIG. 6 and with reference to FIG. 5, the communications interface 604 generally represents the hardware, circuitry, logic, firmware and/or other components of the pump control system 600 that are coupled to the pump control module 602 and configured to support communications between the pump control system 600 and the sensing arrangement 504. In this regard, the communications interface 604 may include or otherwise be coupled to one or more transceiver modules capable of supporting wireless communications between the pump control system 520, 600 and the sensing arrangement 504 or another electronic device 106, 108 in an infusion system 100. In other embodiments, the communications interface 604 may be configured to support wired communications to/from the sensing arrangement 504.

The pump control module 602 generally represents the hardware, circuitry, logic, firmware and/or other component of the pump control system 600 that is coupled to the communications interface 604 and configured to determine dosage commands for operating the motor 506 to deliver fluid to the body 501 based on data received from the sensing arrangement 504 and perform various additional tasks, operations, functions and/or operations described herein. For example, in exemplary embodiments, pump control module 602 implements or otherwise executes a command generation application 610 that supports one or more autonomous operating modes and calculates or otherwise determines dosage commands for operating the motor 506 of the infusion device 502 in an autonomous operating mode based at least in part on a current measurement value for a condition in the body 501 of the user.

In a closed-loop operating mode, the command generation application 610 may determine a dosage command for operating the motor 506 to deliver insulin to the body 501 of the user based at least in part on the current glucose measurement value most recently received from the sensing arrangement 504 to regulate the user's blood glucose level to a target reference glucose value. Additionally, the command generation application 610 may generate dosage commands for boluses that are manually-initiated or otherwise instructed by a user via a user interface element 608. For example, regardless of the operating mode being implemented, the command generation application 610 may determine a dosage command for operating the motor 506 to deliver a bolus of insulin to the body 501 of the user that corresponds to a correction bolus or meal bolus amount selected or otherwise indicated by the user via the user interface element 230, 540, 608.

Still referring to FIG. 6, depending on the embodiment, the pump control module 602 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 602, or in any practical combination thereof. In exemplary embodiments, the pump control module 602 includes or otherwise accesses the data storage element or memory 606, which may be realized using any sort of non-transitory computer-readable medium capable of storing programming instructions for execution by the pump control module 602. The computer-executable programming instructions, when read and executed by the pump control module 602, cause the pump control module 602 to implement or otherwise generate the command generation application 610 and perform the tasks, operations, functions, and processes described in greater detail below.

It should be understood that FIG. 6 is a simplified representation of a pump control system 600 for purposes of explanation and is not intended to limit the subject matter described herein in any way. For example, in some embodiments, the features and/or functionality of the motor control module 512 may be implemented by or otherwise integrated into the pump control system 600 and/or the pump control module 602, for example, by the command generation application 610 converting the dosage command into a corresponding motor command, in which case, the separate motor control module 512 may be absent from an embodiment of the infusion device 502.

Figure 7:
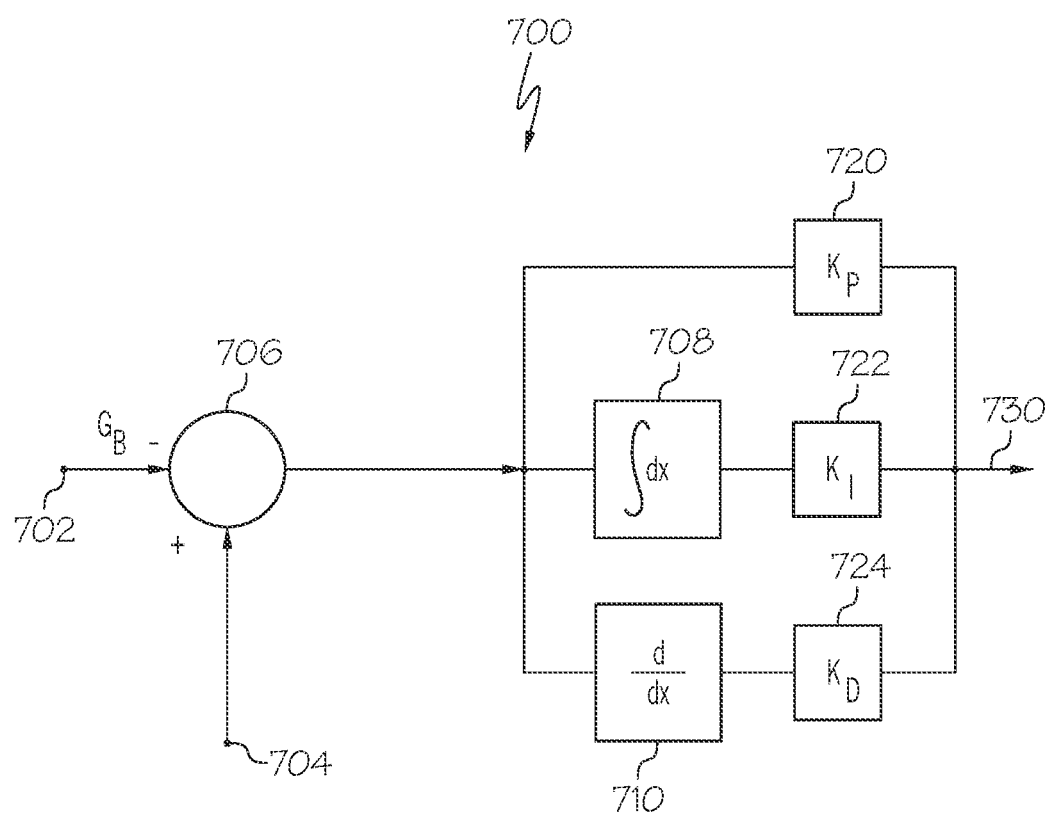
FIG. 7 is a block diagram of a closed-loop control system that may be implemented or otherwise supported by the pump control system in the fluid infusion device of FIG. 5 in one or more exemplary embodiments.

FIG. 7 depicts an exemplary closed-loop control system 700 that may be implemented by a pump control system 520, 600 to provide a closed-loop operating mode that autonomously regulates a condition in the body of a user to a reference (or target) value. It should be appreciated that FIG. 7 is a simplified representation of the control system 700 for purposes of explanation and is not intended to limit the subject matter described herein in any way.

In exemplary embodiments, the control system 700 receives or otherwise obtains a target glucose value at input 702. In some embodiments, the target glucose value may be stored or otherwise maintained by the infusion device 502 (e.g., in memory 606), however, in some alternative embodiments, the target value may be received from an external component (e.g., CCD 106 and/or computer 108). In one or more embodiments, the target glucose value may be dynamically calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 700 also receives or otherwise obtains a current glucose measurement value (e.g., the most recently obtained sensor glucose value) from the sensing arrangement 504 at input 704. The illustrated control system 700 implements or otherwise provides proportional-integral-derivative (PID) control to determine or otherwise generate delivery commands for operating the motor 510 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 702 and the measured glucose level at input 704 to generate or otherwise determine a dosage (or delivery) command provided at output 730. Based on that delivery command, the motor control module 512 operates the motor 510 to deliver insulin to the body of the user to influence the user's glucose level, and thereby reduce the difference between a subsequently measured glucose level and the target glucose level.

The illustrated control system 700 includes or otherwise implements a summation block 706 configured to determine a difference between the target value obtained at input 702 and the measured value obtained from the sensing arrangement 504 at input 704, for example, by subtracting the target value from the measured value. The output of the summation block 706 represents the difference between the measured and target values, which is then provided to each of a proportional term path, an integral term path, and a derivative term path. The proportional term path includes a gain block 720 that multiplies the difference by a proportional gain coefficient, $K_P$, to obtain the proportional term. The integral term path includes an integration block 708 that integrates the difference and a gain block 722 that multiplies the integrated difference by an integral gain coefficient, $K_I$, to obtain the integral term. The derivative term path includes a derivative block 710 that determines the derivative of the difference and a gain block 724 that multiplies the derivative of the difference by a derivative gain coefficient, $K_D$, to obtain the derivative term. The proportional term, the integral term, and the derivative term are then added or otherwise combined to obtain a delivery command that is utilized to operate the motor at output 730. Various implementation details pertaining to closed-loop PID control and determine gain coefficients are described in greater detail in U.S. Pat. No. 7,402,153, which is incorporated by reference.

In one or more exemplary embodiments, the PID gain coefficients are user-specific (or patient-specific) and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 502. The PID gain coefficients may be maintained by the memory 606 accessible to the pump control module 602. In this regard, the memory 606 may include a plurality of registers associated with the control parameters for the PID control. For example, a first parameter register may store the target glucose value and be accessed by or otherwise coupled to the summation block 706 at input 702, and similarly, a second parameter register accessed by the proportional gain block 720 may store the proportional gain coefficient, a third parameter register accessed by the integration gain block 722 may store the integration gain coefficient, and a fourth parameter register accessed by the derivative gain block 724 may store the derivative gain coefficient.

Site Rotation Recommendations

As described above, in exemplary embodiments described herein, the current site location associated with a sensing arrangement 104, 504 is utilized to provide feedback or other recommendations regarding use of the current sensor site and/or other potential sensor sites. For example, when one or more performance metrics associated with operation of an infusion device 102, 200, 502 using sensed glucose measurements obtained at the current sensor site falls below a threshold, a notification may be generated or otherwise provided that indicates, to a user, that the sensor site associated with the sensing arrangement 104, 504 should be changed, or alternatively, that a new or subsequent instance of the sensing arrangement 104, 504 should be located at a different sensor site location. Additionally, based on historical site location information, one or more recommended sensor site locations different from the current site location may be recommended. In some embodiments, contextual information corresponding to anticipated activity by the user (e.g., anticipated exercise, meals, or the like) during the remaining lifetime of the sensing arrangement 104, 504 may be utilized to refine the sensor site recommendations based on correlations between historical performance metrics associated with a sensor site and the anticipated operating context.

It should be noted that sensor site feedback may be provided using any number of devices of an infusion system 100, 500. For example, one or more graphical user interface (GUI) notifications may be generated or provided on any one of the infusion device 102, 200, 502 (e.g., display element 226, user interface element 540, 608, or the like), the sensing arrangement 104, 504, the computer 106, and/or the CCD 108. That said, for purposes of explanation, the subject matter may be described herein primarily in the context of the pump control system 520, 600 of the infusion device 102, 200, 502; however, it should be appreciated that various aspects of the processes described below in the context of FIGS. 8-10 could be implemented or supported by any number of the other electronic devices in an infusion system 100, 500, and the subject matter described herein is not necessarily limited to implementation by an infusion device 102, 200, 502.

Figure 8:
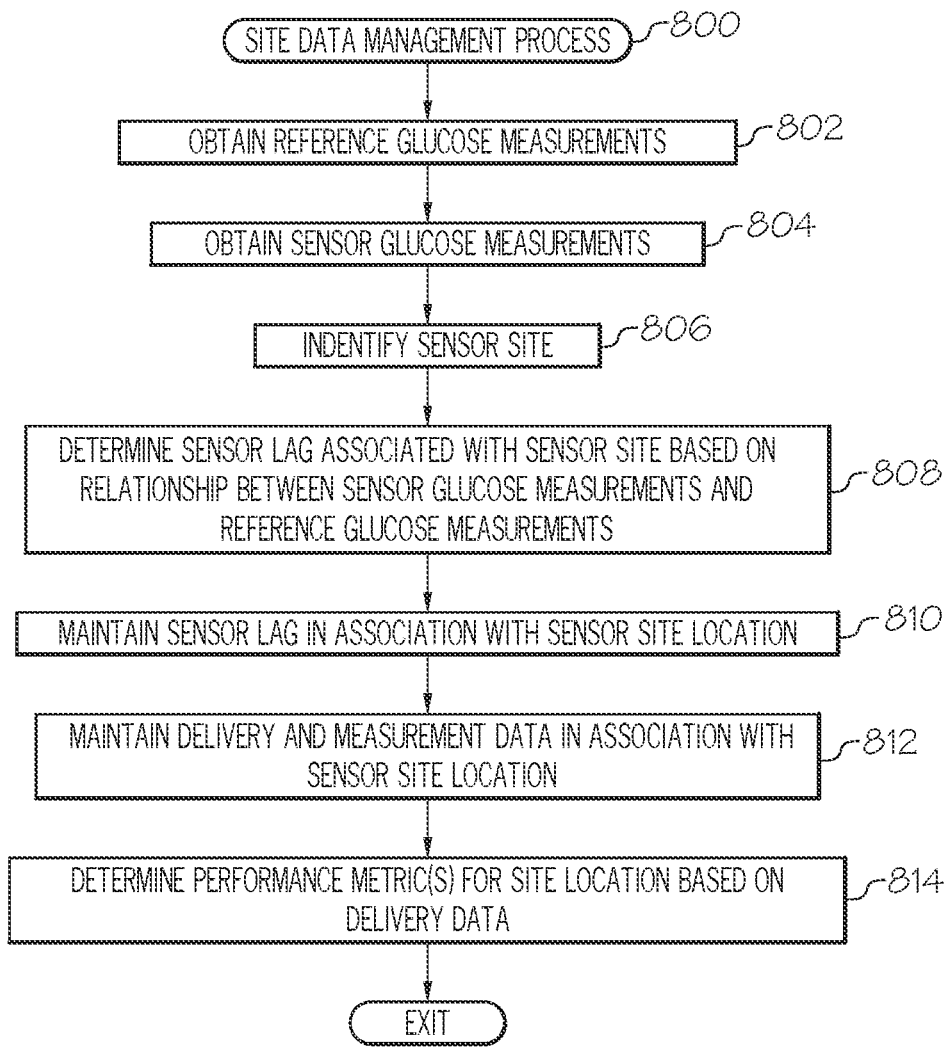
FIG. 8 is a flow diagram of an exemplary site data management process suitable for use with the control system of FIG. 5 in one or more exemplary embodiments.

FIG. 8 depicts an exemplary site data management process 800 suitable for implementation by a control system associated with an electronic device, such as a control system 520, 600 in a infusion device 102, 200, 502, to establish associations between the lag associated with sensor glucose measurements, sensor site locations, performance metrics, and other historical data associated with prior instances of sensing arrangements 104, 504 utilized at different sensor sites for purposes of automatically detecting the sensor site currently in use, providing sensor site recommendations or other site rotation feedback information, and adjusting one or more aspects of autonomous operation of the infusion device to account for the current sensor site, as described in greater detail below in the context of FIGS.

9-10. The various tasks performed in connection with the site data management process 800 may be performed by hardware, firmware, software executed by processing circuitry, or any combination thereof. For illustrative purposes, the following description refers to elements mentioned above in connection with FIGS. 1-7. In practice, portions of the site data management process 800 may be performed by different elements of an infusion system, however, for purposes of explanation, the site data management process 800 may be described herein primarily in the context of the infusion device 502, the pump control system 520, 600, and/or the pump control module 602. It should be appreciated that the site data management process 800 may include any number of additional or alternative tasks, the tasks need not be performed in the illustrated order and/or the tasks may be performed concurrently, and/or the site data management process 800 may be incorporated into a more comprehensive procedure or process having additional functionality not described in detail herein. Moreover, one or more of the tasks shown and described in the context of FIG. 8 could be omitted from a practical embodiment of the site data management process 800 as long as the intended overall functionality remains intact.

The illustrated site data management process 800 initializes or begins by obtaining one or more reference blood glucose measurements for the user and obtaining a plurality of sensor glucose measurements for the user (tasks 802, 804). For example, the pump control system 520, 600 may receive, from the blood glucose meter 530, one or more reference blood glucose measurement values corresponding to the current glucose level in the plasma compartment in the body of the user at the time of sampling, which, in turn, may be stored or otherwise maintained (e.g., in memory 606) and utilized to calibrate signals received from the sensing arrangement 104, 504. Additionally, the pump control system 520, 600 receives sensor glucose measurements from the sensing arrangement 104, 504 corresponding to the glucose level in the interstitial compartment in the body of the user for the time period contemporaneous to or following the time associated with the reference blood glucose measurement values.

The site data management process 800 continues by identifying a current sensor site location (task 806). In this regard, in some embodiments, each time a sensing arrangement 104, 504 is inserted or otherwise deployed at a new sensor site location, a user may manipulate a user interface 540, 608 to input or otherwise provide indication of the sensor site to be associated with the sensed measurement values. That said, in other embodiments, the current sensor site may be automatically detected or identified when sufficient historical sensor site data exists after an initial setup or training phase, for example, as described in greater detail below in the context of FIG. 9.

The site data management process 800 continues by calculating or otherwise determining an amount of sensor lag associated with the current sensor site based on the relationship between the reference blood glucose measurement(s) and the sensor glucose measurements and storing or otherwise maintaining an association between the sensor lag value and the current sensor site (tasks 808, 810). In this regard, the sensor lag may be determined by correlating the sensor glucose measurements to the blood glucose measurements by shifting the time associated with the sensor glucose measurements until the sensor glucose measurements align with the blood glucose measurements. The amount of time shifting corresponds to the time delay or lag associated with the sensor glucose measurements, which, in turn, may be stored or otherwise maintained in association with an identifier for the current sensor site location.

In one embodiment, the sensor glucose measurements and the blood glucose measurements are interpolated to provide corresponding estimated samples having the same sampling frequency that define representative digital signals that may be used for comparisons. For example, blood glucose measurements obtained every 10 to 15 minutes can be interpolated using a cubic interpolation method to create representative samples of the user's plasma glucose level having a sampling frequency of one sample per minute (e.g., representative samples at one minute intervals). Similarly, if sensor glucose measurements are obtained every 5 minutes, a cubic interpolation method may be utilized to create representative samples of the user's interstitial glucose level having a sampling frequency of one sample per minute. The representative interstitial glucose samples and the representative blood glucose samples are associated or otherwise aligned based on the effective sampling time associated with the representative samples.

In exemplary embodiments, time shifted versions of the interstitial glucose signal defined by the interstitial glucose samples are determined, and each time shifted version is compared to the representative blood glucose samples, and one or more correlation coefficients associated with each time shifted interstitial glucose signal are calculated. For example, the time shifted versions of the interstitial glucose signal may be represented as $\text{isig\_shifted}_{tshift}=\text{isig\_bg}[i+tshift]$, where i is an integer that ranges from 1 to the length of the representative interstitial glucose signal aligned with the representative blood glucose signal, tshift is the amount of delay or time shifting, and isig_bg represents the representative interstitial glucose signal aligned with the representative blood glucose signal. In one embodiment, tshift is an integer and ranges from 1 to 20 minutes to obtain 20 different time shifted versions of the interstitial glucose signal, though larger amounts of time shifts may be utilized in the event of sensor site locations having potentially longer delays.

For each time shifted version of the interstitial glucose signal ($\text{isig\_shifted}_{tshift}$), a correlation coefficient associated with that amount of time shifting ($\text{corrCoeff}_{tshift}$) may be calculated based on the covariance between the time shifted interstitial glucose signal and the standard deviations associated with the signals using the following equation: $\text{corrCoeff}_{tshift}=((\text{covar}(\text{isig\_shifted}_{tshift},\text{bg})+\text{corrConst})/((\text{std}(\text{isig\_shifted}_{tshift})\times\text{std}(\text{bg}))+\text{corrConst})$, where bg is the representative blood glucose signal corresponding to the representative blood glucose samples and corrConst is a constant value, which, in one embodiment is chosen to be equal to 0.5. Calculating a correlation coefficient for each time shifted interstitial glucose signal results in an array of values, from which the time shifted interstitial glucose signal having the highest or greatest correlation coefficient associated therewith may be identified. Once the time shifted interstitial glucose signal having the highest correlation coefficient value is identified, the amount of delay or time shifting associated with that signal (tshift) is identified as the lag associated with the current sensor site and stored or otherwise maintained in association with the current sensor site.

Still referring to FIG. 8, in the illustrated embodiment, the site data management process 800 continues by storing or otherwise maintaining delivery data and sensor glucose measurement data in association with the current sensor site location and calculates or otherwise determines one or more performance metrics associated with the current sensor site location (tasks 812, 814). In this regard, the pump control system 520, 600 may store or otherwise maintain information regarding meal boluses and other delivery data (e.g., timing and amounts of insulin delivered) associated with operation of the infusion device 102, 200, 502 using the sensing arrangement 104, 504 at the current site location along with sensor glucose measurements obtained from the sensing arrangement 104, 504. Based on the delivery data and/or the measurement data, the pump control system 520, 600 calculates or otherwise determines one or more metrics indicative of the performance of the infusion device 102, 200, 502 with respect to the glycemic control provided for the user when the infusion device 102, 200, 502 utilizes the sensor glucose measurements for the current sensor site. For example, the pump control system 520, 600 may calculate or otherwise determine a percentage of time the sensor glucose measurements are in a hypoglycemic range or below a threshold value (e.g., less than 70 mg/dL), a percentage of time the sensor glucose measurements are in a hyperglycemic range or above a threshold value (e.g., greater than 180 mg/dL), a percentage of time the sensor glucose measurements are in a euglycemic range or between threshold values (e.g., between 70 mg/dL and 180 mg/dL), a number or frequency of glycemic excursions, one or more metrics of glycemic variability (e.g., standard deviations, variances, or the like associated with the sensor glucose measurements), a number of times or duration of time delivery was suspended, and the like.

The performance metrics associated with the current instance of the sensing arrangement 104, 504 at the current sensor site location may be stored in association with the current sensor site location to facilitate generating sensor site location recommendations, as described in greater detail below in the context of FIG. 9. Additionally, in some embodiments, additional operational context information may be stored or maintained in association with the delivery and measurement data for the current instance of the sensing arrangement 104, 504 at the current sensor site location. In this regard, a user may manipulate a user interface 540, 608 to input or otherwise provide indication of exercise, stress, or other activities he or she engaged in during autonomous operation of the infusion device 102, 200, 502 while the current sensor site location is utilized, identify meal types or amounts, or the like, which, in turn, may be utilized to establish correlations between the performance of a particular sensor site location and operational contexts for purposes of sensor site location recommendations.

Figure 9:
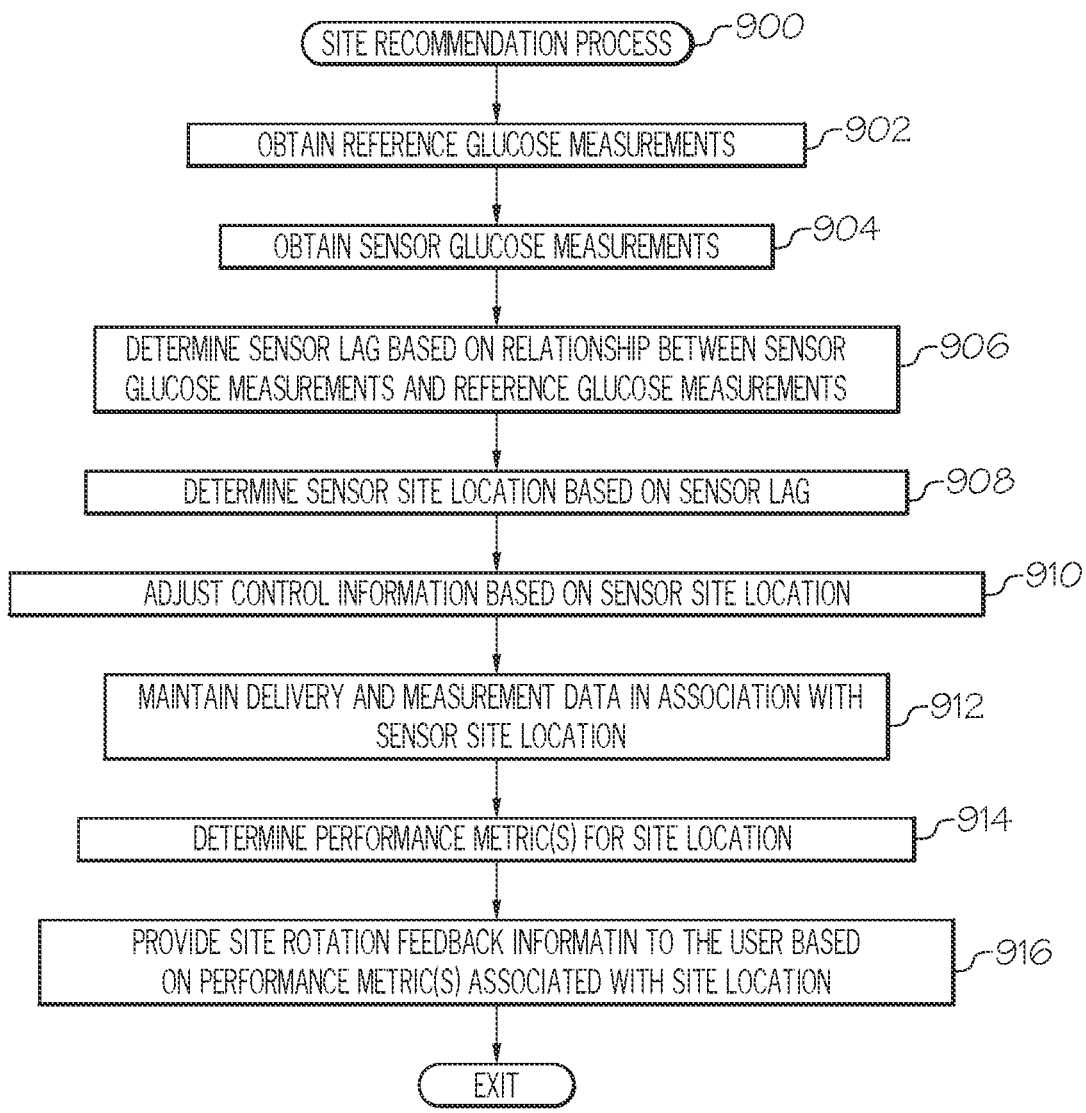
FIG. 9 is a flow diagram of an exemplary site recommendation process suitable for use with the control system of FIG. 5 in conjunction with the site data management process of FIG. 8 in one or more exemplary embodiments.

FIG. 9 depicts an exemplary site recommendation process 900 suitable for implementation by a control system associated with an electronic device, such as a control system 520, 600 in an infusion device 102, 200, 502, to provide sensor site recommendations or other site rotation feedback information. The various tasks performed in connection with the site recommendation process 900 may be performed by hardware, firmware, software executed by processing circuitry, or any combination thereof. For illustrative purposes, the following description refers to elements mentioned above in connection with FIGS. 1-7. In practice, portions of the site recommendation process 900 may be performed by different elements of an infusion system, however, for purposes of explanation, the site recommendation process 900 may be described herein primarily in the context of the infusion device 502, the pump control system 520, 600, and/or the pump control module 602. It should be appreciated that the site recommendation process 900 may include any number of additional or alternative tasks, the tasks need not be performed in the illustrated order and/or the tasks may be performed concurrently, and/or the site recommendation process 900 may be incorporated into a more comprehensive procedure or process having additional functionality not described in detail herein. Moreover, one or more of the tasks shown and described in the context of FIG. 9 could be omitted from a practical embodiment of the site recommendation process 900 as long as the intended overall functionality remains intact.

In a similar manner as described above, the site recommendation process 900 initializes or begins by obtaining one or more reference blood glucose measurements for the user and obtaining a plurality of sensor glucose measurements for the user (tasks 902, 904). For example, when a new instance of a sensing arrangement 104, 504 is inserted or attached to the body of the user, the user may manipulate the blood glucose meter 530 to obtain one or more reference blood glucose measurement values for calibrating the new sensing arrangement 104, 504. The pump control system 520, 600 receives, from the blood glucose meter 530, the reference blood glucose measurement values corresponding to the current blood glucose level and stores or otherwise maintains (e.g., in memory 606) the measurement values for calibrating the sensing arrangement 104, 504 based on one or more sensor glucose measurement values obtained after the reference blood glucose measurements.

The site recommendation process 900 also calculates or otherwise determines a sensor lag associated with the current sensor site location based on the relationship between the reference blood glucose measurement(s) and the sensor glucose measurements (task 906). In this regard, in a similar manner as described above (e.g., task 808), the sensor glucose measurements are correlated to the blood glucose measurements to identify an amount of time by which the sensor glucose measurements lag the blood glucose level. Based on the sensor lag associated with the current sensor site location, the site recommendation process 900 automatically detects or otherwise identifies the current sensor site location (task 908). For example, using the stored historical data maintaining an association between sensor lag and site locations (e.g., task 810), the pump control system 520, 600 may detect or otherwise identify the current sensor site location based on the entry for a site location having an associated lag time that is closest to or equal to the calculated delay time for the current sensor site location. That said, in other embodiments, may manipulate a user interface 540, 608 to input or otherwise provide indication of the current sensor site location in lieu of the automatic detection.

Still referring to FIG. 9, in one or more embodiments, the site recommendation process 900 continues by modifying or otherwise adjusting control information used to autonomously operate the infusion device based on the current sensor site location (task 910). As described in greater detail below in the context of FIG. 10, in one or more embodiments, the pump control system 520, 600 may dynamically update the calibration factor used to convert electrical signals output by the sensing element of the sensing arrangement 104, 504 into a corresponding calibrated sensor glucose measurement value. In other embodiments, the values of one or more other control parameters may be adjusted to tailor the responsiveness of the control system to account for the delay associated with the sensed glucose values. For example, the value of one or more PID gain coefficients 720, 722, 724 may be scaled up or down to increase or decrease the responsiveness of the closed-loop control system 700 to account for the lag associated with the input 704 in a manner that reduces the likelihood of a hypoglycemic or hyperglycemic event. In yet other embodiments, alerting thresholds, delivery suspension thresholds, or other parameters to account for the sensor lag in a manner that improves glycemic control or enhances the user experience (e.g., by avoiding generating unnecessary or non-actionable alerts).

In a similar manner as described above (e.g., tasks 812, 814), the site recommendation process 900 also stores or otherwise maintains delivery data and sensor glucose measurement data in association with the current sensor site location and calculates or otherwise determines one or more performance metrics associated with the current sensor site location (tasks 912, 914). Based on the performance metrics, the site recommendation process 900 generates or otherwise provides one or more user notifications regarding the sensor site rotation (task 916). For example, the pump control system 520, 600 may generate or otherwise provide a graphical representation of the current values for the various performance metrics (e.g., in response to a user interacting with a GUI display to review sensor performance), thereby providing guidance regarding performance of the current sensor site location. In exemplary embodiments, when current values of one or more of the performance metrics are less than a threshold value (e.g., a replacement threshold or a rotation threshold), the pump control system 520, 600 generates or otherwise provides a graphical indication that the sensing arrangement 104, 504 should be replaced or rotated.

In one embodiment, the pump control system 520, 600 accesses the historical performance metrics associated with previous instances of the sensing arrangement 104, 504 and previously used sensor site locations to identify or otherwise determine which sensor site locations other than the current sensor site location achieve the best performance. For example, the pump control system 520, 600 may generate a prioritized list of sensor site locations based on historical performance metrics for previous sensor sites and operating instances (e.g., tasks 814, 914) for use in subsequently recommending a sensor site location. In one embodiment, the sensor site locations are scored or otherwise graded, for example, by calculating a performance score or metric for each sensor site location as a weighted sum of the averaged individual performance metrics for that site, which, in turn, may be utilized to rank or sort sensor site locations by performance score. Thus, the sensor site locations having the best performance may be prioritized over others. Additionally, different site prioritization criteria may be input or otherwise specified by the user and utilized to generate personalized site rotation recommendations based on the user's site rotation preferences in a manner that augments or overrides performance-based rankings. For example, the user may input or otherwise provide a listing of his or her preferred sensor site locations, so that his or her preferred sensor site locations are more highly or more frequently recommended. In this regard, in some embodiments, the pump control system 520, 600 may generate one or more GUI displays corresponding to a site rotation wizard that request input from the user regarding anticipated meals, exercise, or other activities to tailor the recommended sensor sites based on the anticipated operating context. For example, the pump control system 520, 600 may rank the different sensor site locations according to which ones historically achieved the best performance under historical operating contexts correlative to the anticipated operating context. It should be noted that there are any number of conceivable ways to score or rank sensor site locations based on historical data, and the subject matter described herein is not intended to be limited to any prioritization, scoring, or ranking scheme.

In one or more embodiments, after a prioritized list of sensor site locations is determined, the pump control system 520, 600 may filter the prioritized list using one or more filtering criteria to identify one or more recommended sensor sites. For example, in one embodiment, the pump control system 520, 600 may apply a time-based filter to exclude, remove, or otherwise filter out any sensor site use within a preceding period of time (e.g., 72 hours, one week, or the like) to allow the tissue at that site location to adequately recover before reuse. In this regard, in some embodiments, the time-based filtering may be specific to each particular sensor site location. For example, one sensor site location may be allowed to be reused only after a period of 48 hours has elapsed, while another sensor site location may be allowed to be reused only after a period of one week has elapsed, and so on.

Additionally, one or more performance-based criteria may also be utilized to filter or remove sensor site locations. For example, based on one or more variables defining the anticipated operating context, the pump control system 520, 600 may filter out a sensor site location based on that sensor site location having an average percentage of time in a euglycemic range when used in a similar operating context. Thus, if a particular sensor site performs poorly for a given operating context, that sensor site location may be filtered based on recognizing that operating context based on input(s) by the user even though that sensor site would be otherwise recommended based on other anticipated operating context variables.

In one embodiment, one or more display criteria may also be utilized to filter the recommended sensor site locations. In this regard, if only a certain number of recommended sensor site locations may be presented or indicated to the user due to limited display area, that number of displayable recommendations may be utilized to filter or exclude the potential sensor site locations to fit the display area. For example, if the display area only allows for three sensor site recommendations to be displayed, the prioritized list of sensor site locations for recommendation may be truncated after the top three highest ranked sensor site locations.

Again, it should be noted that there are any number of conceivable ways to filter, tailor or otherwise narrow recommended sensor site locations, and the subject matter described herein is not intended to be limited to any particular type of filtering scheme. In this regard, the different filtering criteria utilized to generate recommendations can be modified or otherwise provided by the user to provide personalized site rotation recommendations based on the user's preferences or objectives.

Once the recommended sensor site location(s) for replacing or rotating the current instance of the sensing arrangement 104, 504 is identified, the pump control system 520, 600 may generate or otherwise provide an indication of the recommended sensor site location(s), for example, on the display element 226, 540, 608. In some embodiments, the sensor site rotation recommendations generated by the site recommendation process 900 are provided in real-time, for example, by generating or otherwise providing a notification in response to determining one or more of the performance metrics associated with the current sensor site location fall below or otherwise fail to satisfy applicable replacement or rotation thresholds. In other embodiments, the site recommendation process 900 may delay or withhold the sensor site location recommendations until receiving an indication from the user that he or she is about to replace the current sensing arrangement 104, 504 or in response to some other event (e.g., in response to some user interaction, in response to an indication that the user is awake so as not to generate alerts while the user is sleeping, or the like).

Figure 10:
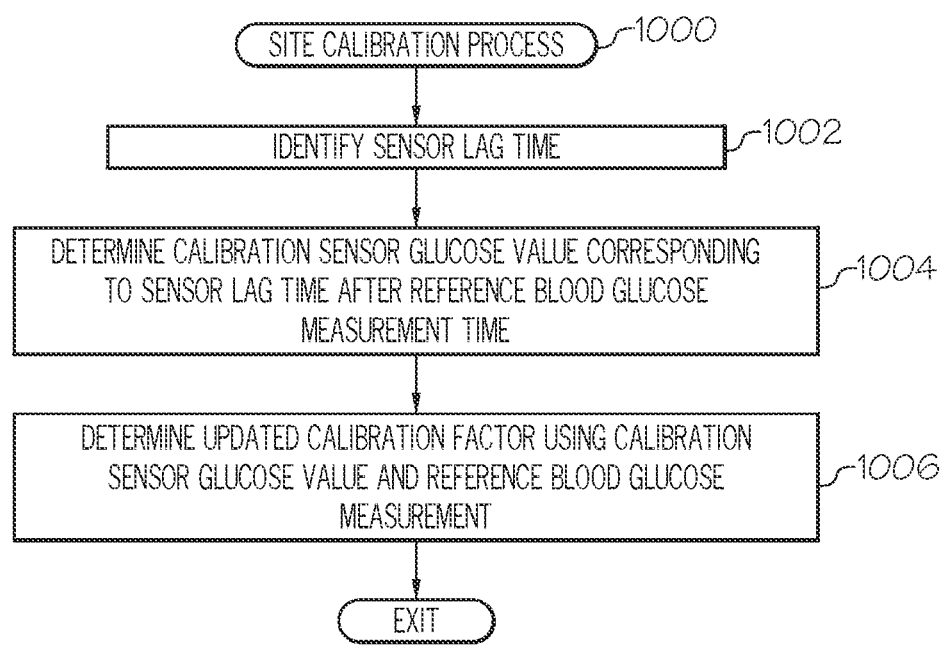
FIG. 10 is a flow diagram of an exemplary site calibration process suitable for use with the control system of FIG. 5 in conjunction with the processes of FIGS. 8 and 9 in one or more exemplary embodiments.

FIG. 10 depicts an exemplary site calibration process 1000 suitable for implementation by a control system 520, 600 of an infusion device 102, 200, 502, to calibrate a sensing arrangement 104, 504 in a manner that is influenced by the current site location associated with the sensing arrangement 104, 504. The various tasks performed in connection with the site calibration process 1000 may be performed by hardware, firmware, software executed by processing circuitry, or any combination thereof. For illustrative purposes, the following description refers to elements mentioned above in connection with FIGS. 1-7. In practice, portions of the site calibration process 1000 may be performed by different elements of an infusion system, however, for purposes of explanation, the site calibration process 1000 may be described herein primarily in the context of the infusion device 502, the pump control system 520, 600, and/or the pump control module 602. It should be appreciated that the site calibration process 1000 may include any number of additional or alternative tasks, the tasks need not be performed in the illustrated order and/or the tasks may be performed concurrently, and/or the site calibration process 1000 may be incorporated into a more comprehensive procedure or process having additional functionality not described in detail herein. Moreover, one or more of the tasks shown and described in the context of FIG. 10 could be omitted from a practical embodiment of the site calibration process 1000 as long as the intended overall functionality remains intact.

The site calibration process 1000 may be initiated or otherwise performed in response to replacement or rotation of a sensing arrangement to dynamically recalibrate the control system for the current sensor site location. The site calibration process 1000 calculates or otherwise determines the amount of lag time or delay associated with the sensor measurement values and then determines a sensor measurement value to be utilized for determining the current calibration factor based on that sensor lag time (tasks 1002, 1004). For example, as described above, based on one or more reference blood glucose measurements and corresponding sensor glucose measurements, the amount of time by which the sensor glucose measurements lag the user's blood glucose may be determined (e.g., tasks 902, 904, 906). Based on that sensor lag time, the pump control system 520, 600 determines corresponding sensor measurement values that follow or succeed the reference blood glucose measurements by that amount of time. In this regard, when the sensor lag time does not align with a discrete sensor measurement value, one or more sensor measurement values following each respective blood glucose measurement value may be interpolated, extrapolated, or otherwise combined to determine an estimated sensor measurement value at that lag time after the respective blood glucose measurement value was obtained. For example, if the sensor lag time is identified as 5 minutes and the nearest available sensor measurement values were obtained from the sensing arrangement 504 at 4 minutes and 6 minutes after a reference blood glucose measurement value was obtained via the blood glucose meter 530, those two sensor glucose measurement values may be averaged to arrive at an estimated sensor glucose measurement value lagging that blood glucose measurement by the sensor lag time.

After identifying the sensor glucose measurement value(s) lagging the reference blood glucose measurement(s) by the sensor lag time, site calibration process 1000 dynamically updates the sensor calibration factor using the identified sensor glucose measurement value(s) (task 1006). The pump control system 520, 600 calculates or otherwise determines a scaling factor to convert the sampled electrical output signal from the sensing arrangement 504 into a corresponding calibrated measurement value by dividing the reference blood glucose measurement(s) by their associated uncalibrated sensor glucose measurement value(s) (or estimates thereof) that lag the respective reference blood glucose measurement(s) by the sensor lag time. In this regard, the pump control system 520, 600 may dynamically update the sensor calibration factor in response to detecting the current sensor site location and the lag time associated therewith. For example, a default lag value (e.g., 15 minutes) may be utilized for determining the calibration factor absent identification of the sensor lag time. Thus, until sufficient reference blood glucose measurement(s) have been determined to allow the current sensor site location and corresponding sensor lag time to be identified, the pump control system 520, 600 may utilize a temporary calibration factor to enable the control system 500 to autonomously operate the infusion device 502 during the interim time period based on the relationship between the reference blood glucose measurement(s) and the uncalibrated sensor glucose measurement(s) (or estimates thereof) lagging those reference blood glucose measurement(s) by the default lag time (e.g., 15 minutes). Thereafter, in response to detecting the current sensor site location and/or the current sensor lag, the pump control system 520, 600 may dynamically recalibrate the control system 500 by recalculating the calibration factor using different uncalibrated sensor glucose measurement(s) (or estimates thereof) that lag the reference blood glucose measurement(s) by the determined sensor lag time associated with the current sensor site location.

Figure 11:
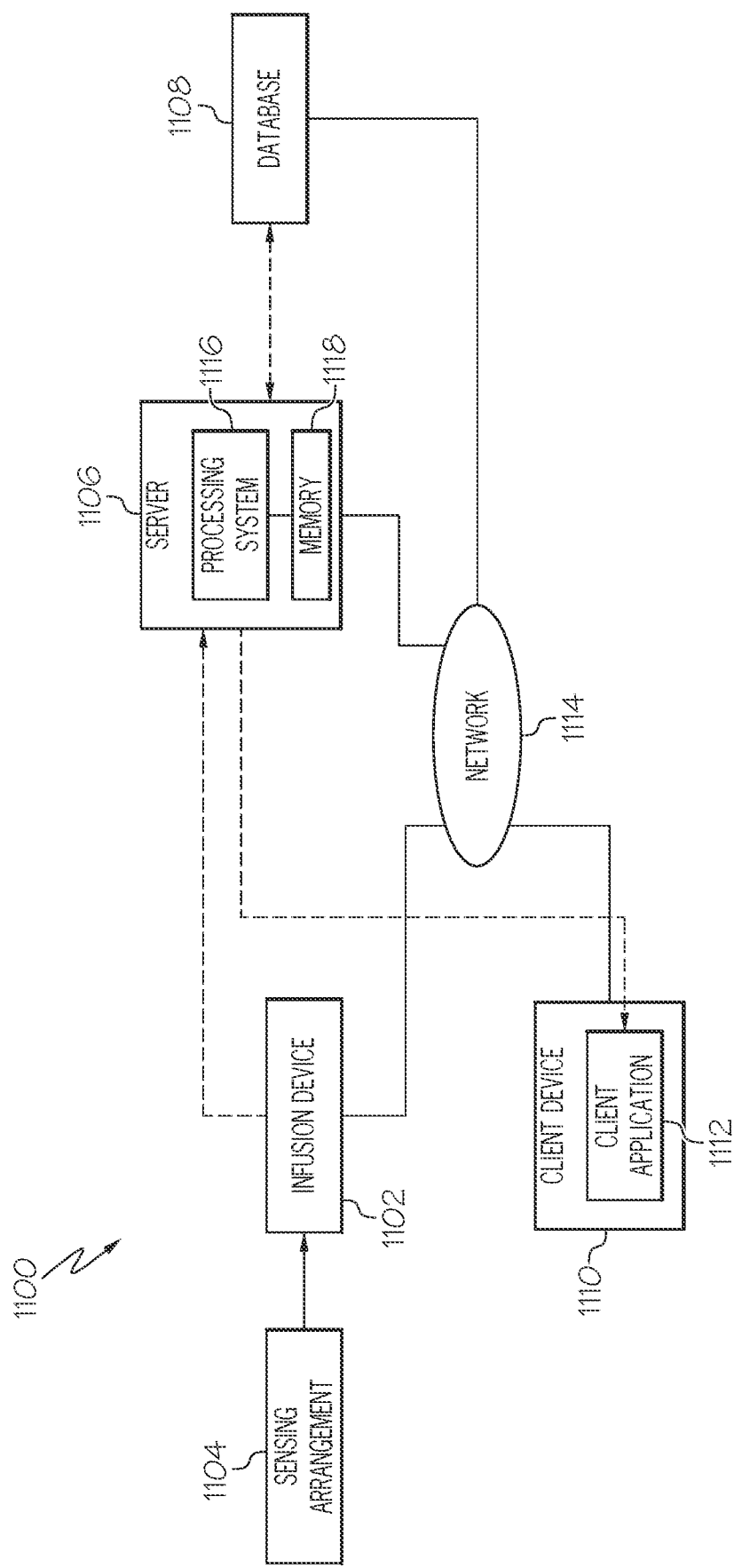
FIG. 11 is a block diagram of an exemplary patient management system capable of supporting one or more of the processes of FIGS. 8-10 in one or more exemplary embodiments.

FIG. 11 depicts an exemplary embodiment of a patient management system 1100 suitable for supporting one or more of the processes 800, 900, 1000 described above. The patient management system 1100 includes an infusion device 1102 (e.g., infusion device 102, 200, 502) that is communicatively coupled to a sensing arrangement 1104 (e.g., sensing arrangement 104, 504) to obtain measurement data indicative of a physiological condition in the body of a patient, such as sensor glucose measurement values. As described above, in one or more exemplary embodiments, the infusion device 1102 operates autonomously to regulate the patient's glucose level based on the sensor glucose measurement values received from the sensing arrangement 1104. It should be appreciated that FIG. 11 depicts a simplified representation of a patient management system 1100 for purposes of explanation and is not intended to limit the subject matter described herein in any way.

In the illustrated embodiment, the infusion device 1102 periodically uploads or otherwise transmits the measurement data (e.g., sensor glucose measurement values, reference blood glucose measurement values, and timestamps associated therewith) to a remote device 1106 via a communications network 1114, such as a wired and/or wireless computer network, a cellular network, a mobile broadband network, a radio network, or the like. That said, in other embodiments, the sensing arrangement 1104 may be communicatively coupled to the communications network 1114 to periodically upload or otherwise transmit measurement data to the remote device 1106 via the communications network 1114 independent of the infusion device 1102. Additionally, the infusion device 1102 may also upload delivery data and/or other information indicative of the amount of fluid delivered by the infusion device and the timing of fluid delivery, which may include information pertaining to the amount and timing of manually-initiated boluses. Some examples of an infusion device uploading measurement and delivery data to a remote device are described in United States Patent Application Publication Nos. 2015/0057807 and 2015/0057634, which are incorporated by reference herein in their entirety.

The remote device 1106 is coupled to a database 1108 configured to store or otherwise maintain the historical measurement and delivery data received from the infusion device 1102 in association with a patient associated with the infusion device 1102 (e.g., using unique patient identification information). Additionally, the database 1108 may store or otherwise maintain, in association with a particular patient, a personalized and patient-specific site rotation preferences or other site rotation recommendation criteria or parameters. In the embodiment of FIG. 11, the remote device 1106 generally represents an electronic device configured to analyze or otherwise monitor the current and historical measurement and delivery data obtained for the patient associated with the infusion device 1102, identify or determine the current sensor site location, and provide corresponding site rotation recommendations to the patient via another electronic device 1110, alternatively referred to herein as a client device. In practice, the remote device 1106 may reside at a location that is physically distinct and/or separate from the infusion device 1102, such as, for example, at a facility that is owned and/or operated by or otherwise affiliated with a manufacturer of the infusion device 1102. For purposes of explanation, but without limitation, the remote device 1106 may alternatively be referred to herein as a server.

The remote device 1106 generally represents a computing system or another combination of processing logic, circuitry, hardware, and/or other components configured to support the processes, tasks, operations, and/or functions described herein. In this regard, the server 1106 includes a processing system 1116, which may be implemented using any suitable processing system and/or device, such as, for example, one or more processors, central processing units (CPUs), controllers, microprocessors, microcontrollers, processing cores and/or other hardware computing resources configured to support the operation of the processing system 1116 described herein. The processing system 1116 may include or otherwise access a data storage element 1118 (or memory) capable of storing programming instructions for execution by the processing system 1116, that, when read and executed, cause processing system 1116 to perform or otherwise support the processes, tasks, operations, and/or functions described herein. Depending on the embodiment, the memory 1118 may be realized as a random access memory (RAM), read only memory (ROM), flash memory, magnetic or optical mass storage, or any other suitable non-transitory short or long term data storage or other computer-readable media, and/or any suitable combination thereof.

The client device 1110 generally represents an electronic device coupled to the network 1114 that may be utilized by a user to access and view data stored in the database 1108 via the server 1106 and/or receive notifications or alerts pertaining to the operation of the infusion device 1102 and/or the sensing arrangement 1104. In practice, the client device 1110 can be realized as any sort of personal computer, mobile telephone, tablet or other network-enabled electronic device that includes a display device, such as a monitor, screen, or another conventional electronic display, capable of graphically presenting data and/or information provided by the server 1106 along with a user input device, such as a keyboard, a mouse, a touchscreen, or the like, capable of receiving input data and/or other information from the user of the client device 1110. In one or more embodiments, the client device 1110 executes a client application 1112 that communicates with the server 1106 via the network 1114 using a networking protocol, such as the hypertext transport protocol (HTTP) or the like.

Referring to FIG. 11 with reference to FIGS. 8-9, in accordance with one or more embodiments, the server 1106 supports the site data management process 800 and the site recommendation process 900 described above. In this regard, the server 1106 may receive, from one or more of the devices 1102, 1104, 1110 (or a blood glucose meter 530) via the network 1114, reference blood glucose measurements (e.g., task 802), sensor glucose measurements (e.g., task 804), and indication of the sensor site locations (e.g., task 806) and calculate or otherwise determine sensor lag times associated with different sensor sites (e.g., tasks 808, 810). In this regard, in addition to patient-specific sensor lag times, in one or more embodiments, the server 1106 may also calculate or otherwise determine average sensor lag times associated with different sensor sites across different patients using data and information received from a plurality of patients. Thus, the average sensor lag times associated with different sensor sites could be utilized in conjunction with the recommendation process 900 and in the absence of any other indication of the current sensor site location for patients that do not have the necessary amount of historical data available in the database 1108 for detecting the current sensor site location using patient-specific sensor lag times (e.g., task 908). The server 1106 may also store or otherwise maintain, in the database 1108, historical delivery data, historical operational context information, historical performance metrics, and the like in association with the sensor site locations (e.g., tasks 812, 814) to support the site recommendation process 900.

Thereafter, when a sensing arrangement 1104 is newly deployed or relocated to a different sensor site location, the server 1106 may utilize the sensor site location lag data to detect or otherwise identify the sensor site location based on subsequently received reference blood glucose measurements and corresponding sensor glucose measurements (e.g., tasks 902, 904). In response to detecting the current sensor site location, the server 1106 may provide a corresponding indication of the current sensor site location and the corresponding sensor lag time to the infusion device 1102 to support the site location calibration process 1000 or otherwise automatically adjust or adapt operation of the infusion device 1102 to account for the current sensor lag time (e.g., tasks 906, 908, 910). The server 1106 may then store the delivery data, operational context information, and the like in association with the detected sensor site location and determine corresponding performance metrics (e.g., tasks 912, 914). Once the performance of the sensing arrangement 1104 indicates that sensor replacement or rotation is desirable, the server 1106 may analyze the delivery data, operational context information, site location performance metrics, and site rotation recommendation preferences or criteria for the user to dynamically determine one or more recommended sensor site locations different from the current sensor site location.

After determining one or more recommended sensor site locations, the server 1106 generates or otherwise provides site rotation feedback to the patient (e.g., task 916). For example, in one embodiment, the server 1106 generates or otherwise provides a site rotation recommendation GUI display on the client device 1110 via the client application 1112 which includes graphical representations or other indications of the sensor site location(s) recommended for use when the patient replaces or rotates the current sensing arrangement 1104. The server 1106 may push or otherwise provide a notification to the patient via the client application 1112 (or a background process associated therewith) which indicates the sensing arrangement 1104 should be replaced along with a GUI element that may be selected by the patient to cause the client application 1112 to present the site rotation recommendation GUI display including the recommended sensor site location(s). In other embodiments, the server 1106 generates or otherwise provides indication of the recommended sensor site locations to the infusion device 1102 and/or the sensing arrangement 1104, which, in turn provide graphical site rotation recommendations and feedback to the patient via their own associated displays.

It should be noted that use of the patient management system 1100 allows for a more comprehensive amount of data regarding sensor site locations to be obtained and stored in the database 1108 for subsequent analysis to refine the ability to automatically detect the current sensor site locations in real-time and improve the quality of the sensor site recommendations. For example, correlations across different patients for different operational contexts, different makes or models of sensing arrangements 1104, and the like for different sensor site locations may be identified and utilized to dynamically adapt the sensor site detection to improve accuracy or reliability (e.g., for patients that otherwise have insufficient amounts of data available), or to otherwise improve the quality of the sensor site recommendations (e.g., based on how a particular sensor site location has performed for similar users given similar operating contexts when insufficient patient-specific data exists for predicting viability of a given sensor site location for an anticipated operational context).

Additionally, in some embodiments, sensor site feedback other than sensor site rotation feedback or recommendations may also be provided. For example, the server 1106 may generate or otherwise provide a site analysis GUI display on the client device 1110 that includes graphical representations of performance metrics associated with the current sensor site location for the current instance of the sensing arrangement 1104 relative to graphical representations of performance metrics associated with other sensor site locations or preceding instances of the sensing arrangement 1104 based on the historical data associated with the patient. Thus, the patient may independently assess the relative performance of different sensor site locations and determine which sensor site location should be utilized next in the rotation in lieu of recommendations that could otherwise be generated by the server 1106, the infusion device 1102, the client application 1112, or the like.

For the sake of brevity, conventional techniques related to glucose sensing and/or monitoring, closed-loop glucose control, sensor calibration, electrical signals and related processing or transmission delays, lag, interference, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A processor-implemented method comprising:
   obtaining measurement data indicative of a physiological condition measured by a sensing arrangement located at a site on a body;
   determining a lag associated with the sensing arrangement based on a relationship between the measurement data and reference data; and
   identifying, based on the lag, the site at which the sensing arrangement is located from a plurality of sites on the body.

2. The method of claim 1, wherein determining the lag comprises:
   generating a plurality of time shifted representations of the measurement data, each time shifted representation having a different respective amount of time shifting;
   determining a respective correlation metric for each time shifted representation based on the reference data; and
   identifying the lag as an amount of time shifting associated with a time shifted representation having a highest value for the correlation metric.

3. The method of claim 1, further comprising:
   determining one or more performance metrics associated with the site on the body; and
   providing sensor site feedback in a manner that is influenced by the one or more performance metrics.

4. The method of claim 3, wherein determining the one or more performance metrics comprises calculating a performance metric comprising one of a percentage of time the measurement data is in a hypoglycemic range below a threshold value, a percentage of time the measurement data is in a hyperglycemic range above a threshold value, a percentage of time the measurement data is in a euglycemic range, a number or frequency of glycemic excursions, and a glycemic variability metric.

5. The method of claim 3, wherein providing the sensor site feedback comprises indicating a recommended site when one of the one or more performance metrics fails to satisfy a rotation threshold.

6. The method of claim 3, further comprising:
   determining one or more recommended sites that are different from the site,
   wherein providing the sensor site feedback comprises generating a graphical representation of the one or more recommended sites that are different from the site.

7. The method of claim 6, wherein determining the one or more recommended sites comprises determining the one or more recommended sites based on historical data associated with the plurality of sites.

8. The method of claim 6, wherein determining the one or more recommended sites comprises determining the one or more recommended sites based on site recommendation criteria associated with the body.

9. The method of claim 1, further comprising:
determining a calibration factor associated with the measurement data based on the reference data in a manner that is influenced by the lag.

10. The method of claim 1, further comprising:
adjusting one or more control parameters in a manner that is influenced by the lag; and
autonomously operating an infusion device to regulate the physiological condition based on the measurement data, the one or more control parameters, and a target value for the physiological condition.

11. The method of claim 1, wherein the sensing arrangement comprises a continuous glucose monitoring (CGM) sensor.

12. A system comprising:
one or more processors; and
one or more processor-readable storage media storing instructions which, when executed by the one or more processors, cause performance of:
obtaining measurement data indicative of a physiological condition measured by a sensing arrangement located at a site on a body;
determining a lag associated with the sensing arrangement based on a relationship between the measurement data and reference data; and
identifying, based on the lag, the site at which the sensing arrangement is located from a plurality of sites on the body.

13. The system of claim 12, wherein the one or more processor-readable storage media further store instructions which, when executed by the one or more processors, cause performance of:
determining one or more performance metrics associated with the site on the body; and
providing sensor site feedback in a manner that is influenced by the one or more performance metrics.

14. The system of claim 13, wherein determining the one or more performance metrics comprises calculating a performance metric comprising one of a percentage of time the measurement data is in a hypoglycemic range below a threshold value, a percentage of time the measurement data is in a hyperglycemic range above a threshold value, a percentage of time the measurement data is in a euglycemic range, a number or frequency of glycemic excursions, and a glycemic variability metric.

15. The system of claim 13, wherein providing the sensor site feedback comprises indicating a recommended site when the one of the one or more performance metrics fails to satisfy a rotation threshold.

16. The system of claim 13, wherein the one or more processor-readable storage media further store instructions which, when executed by the one or more processors, cause performance of:
determining one or more recommended sites that are different from the site,
wherein providing the sensor site feedback comprises generating a graphical representation of the one or more recommended sites that are different from the site.

17. The system of claim 16, wherein determining the one or more recommended sites comprises determining the one or more recommended sites based on historical data associated with the plurality of sites.

18. The system of claim 16, wherein determining the one or more sites comprises determining the one or more recommended sites based on site recommendation criteria associated with the body.

19. The system of claim 12, wherein the one or more processor-readable storage media further store instructions which, when executed by the one or more processors, cause performance of determining a calibration factor associated with the measurement data based on the reference data in a manner that is influenced by the lag.

20. One or more non-transitory processor-readable storage media storing instructions which, when executed by one or more processors, cause performance of:
obtaining measurement data indicative of a physiological condition measured by a sensing arrangement located at a site on a body;
determining a lag associated with the sensing arrangement based on a relationship between the measurement data and reference data; and
identifying, based on the lag, the site at which the sensing arrangement is located from a plurality of sites on the body.

* * * * *